(12) United States Patent
Skadron et al.

(10) Patent No.: US 11,776,594 B2
(45) Date of Patent: Oct. 3, 2023

(54) SCALABLE IN SITU DRAM-BASED ACCELERATORS AND METHODS OF OPERATING THE SAME

(71) Applicant: University of Virginia Patent Foundation, Charlottesville, VA (US)

(72) Inventors: Kevin Skadron, Charlottesville, VA (US); Marzieh Lenjani, Champaign, IL (US); Abdolrasoul Sharifi, Charlottesville, VA (US); Lingxi Wu, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 17/462,836

(22) Filed: Aug. 31, 2021

(65) Prior Publication Data

US 2023/0072191 A1    Mar. 9, 2023

(51) Int. Cl.
| | | |
|---|---|---|
| *G11C 15/00* | (2006.01) | |
| *G11C 7/10* | (2006.01) | |
| *H03K 19/20* | (2006.01) | |
| *G11C 7/12* | (2006.01) | |

(52) U.S. Cl.
CPC ............ *G11C 7/1087* (2013.01); *G11C 7/106* (2013.01); *G11C 7/12* (2013.01); *H03K 19/20* (2013.01)

(58) Field of Classification Search
CPC .................................................. G11C 15/043
USPC ........................................................ 365/49.12
See application file for complete search history.

(56) References Cited

U.S. PATENT DOCUMENTS

| | | | | |
|---|---|---|---|---|
| 6,487,101 B1 * | 11/2002 | Ashbrook | .............. | G11C 15/04 |
| | | | | 365/49.17 |
| 2016/0140243 A1 * | 5/2016 | Adams | ................ | G06F 16/9535 |
| | | | | 707/706 |
| 2022/0019665 A1 * | 1/2022 | Perry | ...................... | G06F 21/53 |

* cited by examiner

*Primary Examiner* — Hoai V Ho
(74) *Attorney, Agent, or Firm* — Stanek Lemon Crouse & Meeks, P.A.

(57) ABSTRACT

Apparatus includes a plurality of memory cells (e.g., a dynamic random access memory (DRAM)) addressable as rows and columns and a plurality of matching circuits configured to be coupled to respective bit lines associated with the columns A control circuit is configured to store respective reference sequences (e.g., binary-encoded k-mer patterns) in respective ones of the columns, to sequentially provide rows of bits stored in the memory cells and bits of a query to the matching circuits, and to identify one of the reference sequences as corresponding to the query responsive to comparisons by the matching circuits.

18 Claims, 11 Drawing Sheets

SCALABLE IN SITU DRAM-BASED ACCELERATORS AND METHODS OF OPERATING THE SAME

STATEMENT OF GOVERNMENT SUPPORT

This invention was made with government support under Grant No. HR0011-18-3-0004 awarded by the Department of Defense/Defense Advanced Research Projects Agency (DARPA). The government has certain rights in this invention.

BACKGROUND

The field of bioinformatics has enabled significant advances in human health through its contributions to precision medicine, disease surveillance, population genetics, and many other critical applications. The centerpiece of a bioinformatics pipeline is genome sequence comparison and classification, which involve aligning query sequences against references sequences, with the goal of identifying patterns of structural similarity and divergence. While traditional sequence alignment algorithms employ computationally-intensive dynamic programming techniques, there has been a growing shift to a high-performance heuristic-based approach called k-mer matching, that breaks a given query sequence into a set of short subsequences of size k, which are then scanned against a reference database for hits, with the underlying assumption that biologically correlated sequences share many short lengths of exact matches. Owing to their relatively low computational complexity, k-mer matching-based algorithms have been deployed in a wide array of bioinformatics tasks, including but not limited to, population genetics, cancer diagnosis, metagenomics, bacterial typing, and protein classification.

The acceleration of bulk k-mer matching is of paramount importance for two major reasons. First, k-mer matching sits on the critical path of many genome analysis pipelines. FIG. 1 shows the execution breakdown of several important bioinformatics applications geared at performing a variety of different tasks ranging from metagenomics to population genetics. Note that k-mer matching clearly dominates the overall execution time in all applications. Second, modern sequencing technologies generate data at a rate surpassing Moore's Law. In fact, by 2025, the market share of metagenomics alone is expected to reach $1.4 billion, and the amount of data that needs to be analyzed by metagenomics pipelines is projected to surpass that of YouTube and Twitter. To further exemplify the scale of data explosion and processing overhead, consider the case of precision medicine, where a patient's sample can be sequenced in roughly 48 hours on the NovaSeq instrument, producing 10 TB microbiome and human DNA/RNA data. To develop personalized treatment from these samples, this raw sequence data is passed through, often in parallel, various metagenomics stages with k-mer matching on the critical path (e.g., ~68 days on Kraken), graph-based whole genome assembly (e.g., MetaSPAdes), and sequence alignment pipelines (e.g., bowtie2 and HUMAnN2). These tasks play a critical role in combating pandemics and treating antibiotic-resistant infections, saving billions of dollars in health care costs.

However, despite its significance, the acceleration of k-mer matching on modern high-end computing platforms remains a challenge, due to its inherently memory-bound nature, considerably limiting downstream genome analysis tasks from realizing their full potential. In particular, k-mer matching algorithms are typically characterized by random accesses across large memory regions, leading to poor cache behavior, even on high-end servers that feature large last-level caches. The cache-unfriendliness of k-mer matching will continue to get worse with the rapid growth in the size and complexity of genomic databases, making the task a major bottleneck in modern bioinformatics pipelines. This is further exacerbated by the fact that the computation per k-mer lookup is too small to mask the high data access latency, thereby rendering existing compute-centric platforms such as multi-core CPUs and GPUs inadequate for large-scale genome analysis tasks.

Memory-centric solutions to accelerate bioinformatics applications come in a variety of different flavors, but several recent proposals demonstrate that near-data and in-memory processing systems have promising potential to improve the performance and efficiency of large-scale genome analysis tasks, owing to the fact that these applications are increasingly characterized by their high data movement (from memory to the processor) and low computation (within the processor) costs. This work explores the design space for high-performance k-mer matching accelerators that use logic in DRAM as the basis for acceleration, including the most aggressive form of processing-in-memory (PIM), in-situ computing, which allows for the processing of data within row buffers.

The advantage of in-situ computing is that the bandwidth at the row buffer is six orders of magnitude larger than that at the CPU, while the energy for data access is three orders of magnitude lower. However, in-situ computing also introduces several critical challenges. First, in-situ acceleration necessarily requires the tight integration of processing logic with core DRAM components, which has been shown to result in prohibitively high area overheads. In fact, even a highly area-efficient state-of-the-art in-situ accelerator is only half as dense as a regular DRAM. However, most bioinformatics applications typically favor accelerators with larger memory capacity because of their ability to better accommodate the ever-increasing DNA datasets that need to be analyzed within short time budgets. Second, existing in-situ computing solutions rely on multi-row activation and conventional row-wise data mapping to perform bulk Boolean operations of data within row buffers, resulting in substantial loss of throughput and efficiency. Finally, to capitalize on the performance benefit of in-situ computing for k-mer matching, it is imperative that the accelerator is provisioned with an efficient k-mer indexing scheme that avoids query broadcasting, and a mechanism to quickly locate and transfer payloads (e.g., genome taxon records).

The concept of PIM dates back to the 70s. Since then, there have been many proposals integrating heavy logic into 2D planar DRAM dies. These early efforts largely remain at their inception stage due to the challenges of fabricating logic using the DRAM process. Recently, the 3D-stacked technology, which takes a more practical approach by placing a separate logic die underneath the DRAM dies, revitalizes the interests in PIM research. To fully exploit the benefit of 3D-stacked architectures, many domain specific accelerators for graph processing, pointer chasing, and data analytics have been proposed. We plan to evaluate Sieve in 3D-stacked context as future work. Since DRAM-based in-situ accelerators are extensively analyzed in the previous sections, we focus our discussion on non-DRAM-based in-situ and bioinformatics-focused PIM works that share similar interests concerning Sieve.

Non-DRAM-based In-situ Accelerators. NVM- and SRAM-based in-situ accelerators such as Pinatubo and Compute Caches have been proposed.

PIM-based Genomics Accelerators. Recently, PIM has been explored for several algorithm-specific PIM architectures for genomics. For example, GenCache modifies commodity SRAM cache with algorithm-specific operators, achieving energy reduction and speedup for DNA sequence aligners. Medal leverages commodity Load-Reduced Dual-Inline Memory Module (LRDIMM) and augments its data buffers with custom logic to exploit additional bandwidth and parallelism for DNA seeding. Radar provides a high scalability solution for BLAST by mapping seeding and seed-extension onto dense 3D non-volatile memory. However, these efforts are not ideal for k-mer matching. GenCache has hardwired logic in SRAM to compute Shifted Hamming Distance and Myer's Levenshtein Distance, which are not used for k-mer matching. Medal is highly optimized for FM-index based DNA seeding, which relies on different data structures (suffix arrays, accumulative count arrays, occurrence arrays) than those in k-mer matching (associative data structures such as dictionaries). Radar binds seed-extension, a stage irrelevant to k-mer matching, with seeding to maximize speedup.

SUMMARY

Some embodiments provide apparatus including a plurality of memory cells addressable as rows and columns a plurality of matching circuits configured to be coupled to respective bit lines associated with the columns, and a control circuit configured to store respective reference sequences (e.g., binary-encoded k-mer patterns) in respective ones of the columns, to sequentially provide rows of bits stored in the memory cells and bits of a query to the matching circuits, and to identify one of the reference sequences as corresponding to the query responsive to comparisons by the matching circuits.

In some embodiments, the plurality of memory cells may include at least one subarray of a bank of a dynamic random access memory (DRAM). The matching circuits may be coupled to outputs of respective sense amplifiers that feed a row buffer of a subarray of the bank. In some embodiments, the bank may include a plurality of interconnectable subarrays, each subarray having row buffer configured to be coupled to bit lines of an adjacent subarray and the matching circuits being coupled to a row buffer of one of the subarrays. In further embodiments, each of the matching circuits may include an XNOR gate having a first input that receives column entries and a second input that receives bits of the query, an AND gate having a first input coupled to an output of the XNOR gate, and a latch having an input coupled to an output of the AND gate and an output coupled to a second input of the AND gate.

According to further aspects, the control circuit may be configured to terminate provision of rows to the matching circuits responsive to the matching circuits indicating that all of the references sequences lack at least one bit of the query. The control circuit may include respective segment evaluation circuits coupled to respective groups of the matching circuits and configured to generate respective match indicators for respective subgroups of each row of bits provided to the matching circuits. The control circuit may be configured to terminate provision of rows to the matching circuit responsive to the segment evaluation circuits. Each of the segment evaluation circuits may include a plurality of cascaded OR gates that receive inputs from respective ones of the matching circuits and a segment register that receives and stores a value output from the plurality of cascaded OR gates and provides the stored output to another one of the segment evaluation circuits. The control circuit may be configured to latch values in the segment registers of the segment evaluation circuits during each cycle of a sequence of cycles in which the rows are provided to the matching circuits. The control circuit may further include a plurality of secondary segment registers, respective ones of which receive and store the values received and stored by respective ones of the segment registers, and may be configured to identify a column containing a reference sequence corresponding to the query responsive to the secondary segment registers.

Further embodiments provide methods including storing respective reference sequences in respective ones of columns of a plurality of memory cells addressable as rows and columns. Rows of bits stored in the memory cells and bits of a query are sequentially provided to a plurality of matching circuits coupled to respective bit lines associated with the columns. One of the reference sequences is identified as corresponding to the query responsive to comparisons by the matching circuits.

DETAILED DESCRIPTION

Figure 1:
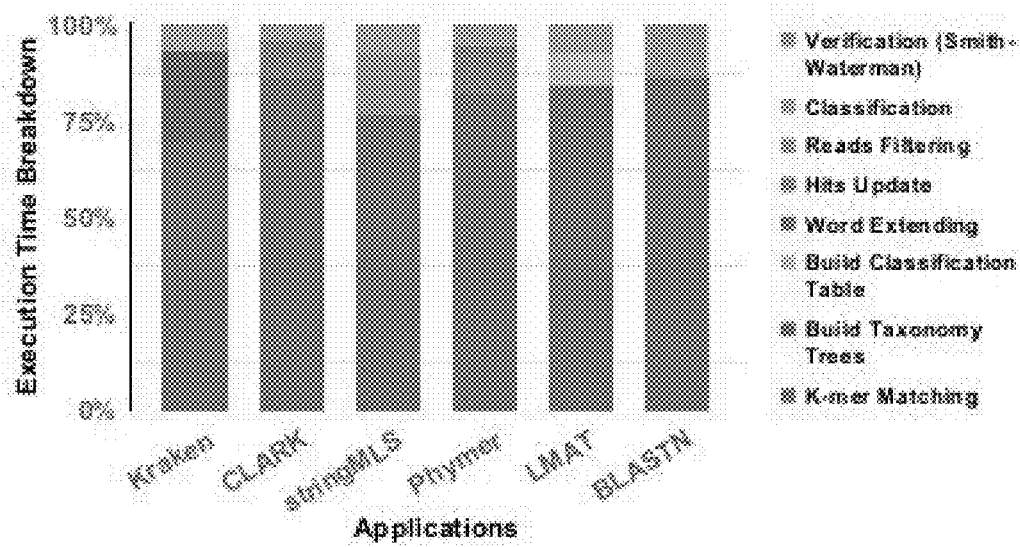
FIG. 1 shows execution breakdown of several conventional bioinformatics applications.

Specific exemplary embodiments of the inventive subject matter now will be described with reference to the accompanying drawings. This inventive subject matter may, however, be embodied in many different forms and should not be construed as limited to the embodiments set forth herein; rather, these embodiments are provided so that this disclosure will be thorough and complete, and will fully convey the scope of the inventive subject matter to those skilled in the art. In the drawings, like numbers refer to like elements. It will be understood that when an element is referred to as being "connected" or "coupled" to another element, it can be directly connected or coupled to the other element or intervening elements may be present. As used herein the term "and/or" includes any and all combinations of one or more of the associated listed items.

The terminology used herein is for the purpose of describing particular embodiments only and is not intended to be limiting of the inventive subject matter. As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive subject matter belongs. It will be further understood that terms, such as those defined in commonly used dictionaries, should be interpreted as having a meaning that is consistent with their meaning in the context of the specification and the relevant art and will not be interpreted in an idealized or overly formal sense unless expressly so defined herein.

This work explores the design space of high-performance in-situ PIM-based k-mer matching accelerators, with the goal of exploiting greater levels of data parallelism, while making minimally intrusive changes to conventional DRAM designs. To this end, we propose Sieve, a set of novel Scalable in-situ DRAM-based accelerator designs for massively parallel k-mer matching. Specifically, we offer three separate designs: Sieve Type-1, Type-2, and Type-3. Each architecture incrementally adds extra hardware complexity to unlock more performance benefits.

The key distinguishing feature of Sieve is the placement of reference k-mers vertically along the bitlines of DRAM chips and subsequently utilizing sequential single-row activation rather than the multi-row activation proposed in prior works, to look up queries against thousands of reference k-mers simultaneously. The column-wise placement of k-mers further allows us to employ a novel Early Termination Mechanism (ETM) that interrupts further row activation upon the successful detection of a k-mer mismatch, thereby considerably alleviating the latency and energy overheads due to serial row activation. To the best of our knowledge, this is the first work to introduce and showcase the effectiveness of such a column-wise data mapping scheme for k-mer matching with early termination, substantially advancing the state-of-the-art in terms of both throughput and efficiency.

By taking advantage of the fact that matching individual k-mers is relatively less complex than most other conventional PIM tasks such as graph processing, in this work, we design a specialized circuit for k-mer matching, with the goal of minimizing the associated hardware cost. We then meticulously explore the design space of an in-situ PIM-based accelerator by placing such custom logic at different levels of the DRAM hierarchy from the chip I/O interface (Type-1) to the subarray level (Type-2/3), with a detailed analysis of the performance-area-complexity trade-offs associated with each Sieve design, and a discussion of system integration issues, deployment models, and thermal concerns. We compare each Sieve design with state-of-the-art k-mer-matching implementations on CPU, GPU, and FPGA, and perform rigorous sensitivity analyses to demonstrate their effectiveness. We show that the processing power of Sieve scales linearly with respect to its storage capacity, considerably enhancing the performance of modern genome analysis pipelines.

This work makes the following major contributions:

We profile a suite of k-mer-matching-intensive workloads, identify their core operations, and explore three novel design points (Sieve Type-1/2/3) to perform in-memory acceleration of k-mer matching. Sieve Type-1 minimizes area overhead, Type-3 maximizes throughput, and Type-2 balances performance and design complexity.

We propose a novel, sequential, single-row activation and column-wise data mapping scheme to replace the multi-row activation and row-wise data mapping paradigm employed by prior art. Further, observing the characteristics of realistic DNA sequence data, we employ a synergistic early termination mechanism to prune DRAM row activation, thereby substantially reducing latency and energy consumption.

We provide an in-depth description of Sieve Type-1/2/3 circuit designs, highlighting our key mechanisms and optimizations geared at meeting the tight area and timing constraints of DRAM architectures.

We propose a PCIe-integrated cloud-based accelerator deployment model for Sieve, and provide a cost analysis to determine whether chip manufacturers, cloud providers, and bioinformatics communities as a whole can receive a net financial benefit by adopting Sieve.

We perform extensive evaluation of Sieve using real-world workloads and datasets. Our most aggressive design provides an average speed up of 210×/35× and an average energy savings of 35×/71× over conventional multi-core-CPU/GPU baselines for k-mer matching.

In this section, we first introduce the k-mer matching procedure and explain why it is a bottleneck stage in conventional architectures. We then provide a brief overview of conventional DRAM architectures.

K-mer Matching in Bioinformatics. A DNA sequence is a series of nucleotide bases commonly denoted by four letters (bases): A, C, G, and T. K-mers are subsequences of size k. Metagenomic algorithms attempt to assign taxonomic labels to genetic fragments (sequences) with unknown origins. A "taxonomic label" is an assignment of a sequence to a particular organism or species. A sequence that is shared by multiple species can only be classified in a more coarse-grained way. Traditionally, this is done by aligning an individual query sequence against reference sequences, which can be prohibitively slow. Processing a metagenomics file containing $10^7$ sequences using an alignment-based BLAST algorithm takes weeks of CPU time. Experts predict that genomics will soon become the most prominent data producer in the next decade, demanding more scalable sequence analysis algorithms and infrastructure. Under these circumstances, alignment-free tools that rely on simple k-mer matching have emerged to aid large-scale genome analysis tasks, owing to the fact that properly labeled k-mers are often sufficient to infer taxonomic and functional information of a sequence.

A typical k-mer-matching-based sequence classifier works as follows. In an offline stage, a reference k-mer database is built, which maps unique k-mer patterns to their taxon labels. For example, if a 5-mer "AACTG" can only be found in the *E. coli* bacteria bacteria sequence, an entry that maps "AACTG" to *E. coli* is stored. At run time, k-mer matching algorithms slide a window of size k across the query sequence, and for each resulting k-mer, they attempt to retrieve the associated taxon label from the database. This process may be described as follows:

```
for (query_seq: query_list){
    kmer_list = [ ]
    payload_list = [ ]
    ... // store k-mers from query_seq
    for (kmer: kmer_list){
        result = query_kmer(kmer, reference k-merset, ...)
        if (result != NULL) // found match, retrieve payload
            payload_list.add(result.payload)
        else
            ... // no match
    }
    ... // classify query_seq using payload_list
}
```

Function query kmer is repeatedly called to search each k-mer in the database. If the query k-mer exists in the database (k-mer hit), its taxon label (payload) is retrieved. Once all k-mers in a query are processed, the taxon labels of the matched k-mers are used to make a final decision on the originating organism for the query sequence. The reference k-mer set itself can be implemented in a number of ways. CLARK and LMAT leverage a hash table, with the k-mer pattern as the key and the taxon label as the value. Kraken uses a more sophisticated data structure that is a hybrid between a hash table and a sorted list, in which k-mers that share the same "signature" are put into the same hash bucket, which is then looked up using binary search. The assumption here is that two adjacent k-mers within a query sequence are likely to share the same "signature", since they overlap by (k−1) bases, and are thereby likely to get indexed into the same bucket.

Since exact matching is inherently faster than calculating the alignment, metagenomic tools that leverage k-mer matching are three orders of magnitude faster than those that use alignment approaches, while maintaining acceptably high accuracy.

Memory Is the Bottleneck for K-mer Matching. First, real-world k-mer matching applications expose limited cache locality. For sequence classifiers that store reference k-mers in a hash table, accessing a hash table can generate a large number of cache misses due to the linked list traversal or repeated hashes (to resolve hash collision). In theory, the hash table/sorted list hybrid can provide better locality, since the k-mer bucket could be already fetched into the cache from the previous k-mer lookup. However, using Kraken and its supplied datasets, we discover that only 8% of consecutive k-mers are indexed into the same bucket. As a result, new buckets are fetched repeatedly from memory to serve search requests. Second, k-mer matching benefits from finer-grained memory access. Each k-mer record is generally around 12 bytes, while each memory access retrieves a cache line of data, which usually serves only one request due to the poor locality, resulting in waste of bandwidth and energy. Third, computational intensity of k-mer matching is too little to mask extended data access latency. Using CLARK as an example, we find that updating counters for matched k-mers is trivial for CPU, while searching k-mers in the database takes many cycles due to cache misses. As a result, CPUs are constantly stalling for data Overall, the memory subsystem is a major bottleneck of k-mer matching.

Our profiling analysis on standard bioinformatics workloads indicates that k-mer matching consistently dominates the execution time (50-80%).

We address the main challenge of designing in-situ k-mer matching accelerators, namely integrating logic into DRAM dies with low hardware overhead. We propose three separate Sieve designs to combat this issue. We then identify the key limitations of prior in-situ work when adapted for k-mer matching and motivate our novel data layout and pattern matching mechanisms Finally, we introduce an Early Termination Mechanism (ETM) to further optimize Sieve by exploiting characteristics of real-world sequence datasets.

DRAM Overhead Concerns. In-situ accelerators can provide dramatic performance gains for memory-intensive applications such as k-mer matching. However, building them with reasonable area overhead is difficult. The sense amplifiers in row buffers are laid out in a pitch-matched manner, and the DRAM layout is carefully optimized to provide high storage density, and therefore, fitting additional logic into the row buffer in a minimally invasive way is non-trivial. Moreover, since the number of metal layers of a DRAM process is substantially smaller than that of the logic process, building complex logic with a DRAM process incurs significant interconnect overhead. Many early attempts that embed processing cores in memory fail because integrating logic into memory reduces yield and raises thermal concerns. Furthermore, DRAM is a commodity whose market is highly sensitive to cost.

However, while Sieve could be employed in main memory, residing in DIMM slots, it can also be deployed on an accelerator card. In either case, Sieve is first and foremost an accelerator, and DRAM is a technology choice selected for this accelerator, for its density and ability to provide high capacity. (Even when deployed on an accelerator card, with the forthcoming CXL standard, it will also be able to serve as part of a NUMA memory system.) We design and implement a set of core k-mer matching operations for Sieve using simple Boolean logic. Sieve has very little hardware overhead compared to other PIM architectures, because k-mer matching, which is mainly accomplished by exact pattern matching, can be supported by a minimal set of Boolean logic.

Trade-offs of Different Sieve Designs. To explore optimal Sieve designs, we compare the placement of the custom k-mer matching logic at three different levels in the DRAM hierarchy: from the I/O interface of the DRAM chips (Sieve Type-1) to the local row buffer of each subarray (Sieve Type-3), and Type-2 as the middle ground where several subarrays share one k-mer matching unit. Recall that a DRAM bank's transistor layout is highly optimized for storage, and inserting extra logic, however minimal, requires significant redesign effort. Type-1 keeps the bank layout intact, and thus is the least intrusive design. However, it suffers from the lowest parallelism and the highest latency because the comparison is restricted to a column of bits rather than the entire row. Sieve Type-2 increases parallelism and energy efficiency over Type-1 by accessing a row of bits. Type-3 leverages recent work on subarray-level parallelism (SALP) and copies k-mer matching logic into all local row buffers. This is our most aggressive design, which has the highest performance potential (measured by the number of bases processed per second per watt), but it comes at the cost of the highest design complexity and hardware overhead.

Novel Data Layout and Pattern Matching Mechanism. We show that our column-wise k-mer data layout and row-wise matching mechanism, combined with early termination outperforms prior in-situ accelerators that rely on multi-row activation and conventional row-wise data mapping. The majority of the k-mer matching workload is exact pattern matching, which can be performed using bulk bitwise AND between two operand DRAM rows. We use Ambit as a baseline. Both Ambit and 1T1C-based DRISA are inspired by the same work for in-situ AND procedure. Thus, their performance for k-mer pattern matching is similar. Ambit performs bulk bitwise AND in reserved DRAM rows (see FIG. 2). Assuming a DNA base is encoded with two bits (by NCBI standard), a common k value of 31, and a typical DRAM row width of 8192 bits, then each row fits 128 k-mer patterns if k-mers are stored in a row-wise manner. To search a query against a group of references, Ambit first copies 128 different reference patterns from the data region to RRef. It then makes 128 copies of the same query in RQuery. Since the target operation is AND, the control row (RCtrl) is populated with 0s (copied from a preset row). Next, a triple-row activation is performed on RRef, RQuery, and RCtrl. Finally, the result bits are copied to another row RResult. One row-wide AND takes 8 row activations and 4 precharge commands, which is 8*tRAS (~35 ns/tRAS)+ 4*tRP (~15 ns/tRP)=~340 ns.

Figure 3:
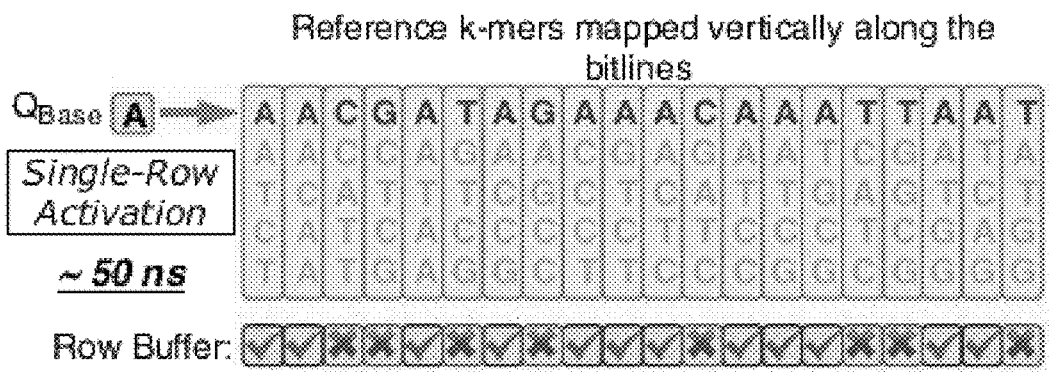
FIG. 3 is a chart illustrating a sequence matching process according to some embodiments of the inventive subject matter.

Sieve does not adopt this multi-row activation paradigm for in-situ pattern matching, and it does not compare a full-length query k-mer against a set of full-length reference k-mers at once. Instead, it compares a query with a more extensive set of references in a shorter time window (1*tRAS+1*tRP=~50 ns), but progresses only one bit at a time (see FIG. 3). Reference bits in Sieve are laid out column-wise, along bitlines. Thus, a single row activation transfers 8K bits into the matchers embedded in row buffers for comparison. Each matcher has a one-bit latch to keep track of the matching result. The next row is activated, and a new batch of reference bits is compared, until ETM (introduced next) interrupts when all latches return zero.

Processing only one bit at a time does not hurt Sieve's performance, because it leverages parallelism across the rows; i.e., it performs 8K comparisons at once. The vertical data layout greatly expands the initial search space (128 reference k-mers to 8192 reference k-mers), and our early termination mechanism (ETM) quickly eliminates most of the candidates after just a few row activations. Besides the latency reduction for each row-wide pattern matching by adopting single-row activation (~340 ns to ~50 ns), Sieve also reduces activation energy, since raising each additional wordline increases the activation energy by 22%. Thus, even if the same data mapping strategy is applied, the multi-row activation-based approach is still slower and less energy efficient than Sieve simply because of the internal data movement. Note that the internal data movements associated with multi-row activation is unavoidable, because the operand rows have to be copied to the designated area. Furthermore, arbitrarily activating three rows inside the DRAM requires a prohibitively large decoder (possibly over 200% area overhead), and activating more than one row could potentially destroy the original values.

The Motivation for Early Termination. Relying on row activation for pattern matching is inefficient. Activating consecutive rows in the same bank results in highly unfavorable DRAM access patterns that are characterized by long delays (due to the increase in the number of row cycles) and high energy costs (row opening dominates DRAM energy consumption).

Figure 4:
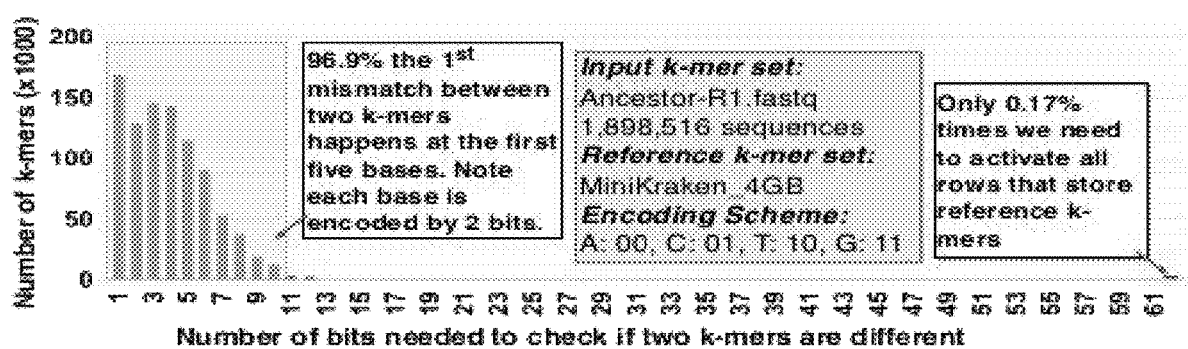
FIG. 4 is a chart illustrating estimated performance of a sequence matching process according to some embodiments.

In this work, we identify a novel optimization opportunity that exploits the concept of the Expected Shared Prefix (ESP), which describes the first mismatch location between two random DNA sequences. On average, for DNA sequences between 1 k and 16 k bases, the first mismatch is known to occur between the sixth and the eighth base. Since Sieve works shorter k-mers (31 bases), the ESP is expected to be even smaller than six, and in fact, our observations support this hypothesis. For random k-mers extracted from metagenomics reads, when matched against reference k-mers, nearly 97% of the first mismatch can be found within the first five bases (first 10 bits if each base is encoded by two bits), as shown in FIG. 4. Our experiments show that ETM enhances the performance of Sieve by 5.2-7.2× and reduces energy consumption by 3.1-6.7×. ETM is described in more detail in Section 4.

Sieve Architecture

In this section, we describe the implementation details of the three Sieve designs. We first introduce Sieve Type-2 and Type-3, because they demonstrate the best performance, and they closely resemble each other. Type-1 is discussed at the end of this section because it diverges slightly from the other two forms of Sieve, and it faces a unique set of issues that are addressed separately. We quantify our discussion using parameters from a Micron DRAM chip datasheet.

Sieve Type-2 and Type-3

Figure 5:
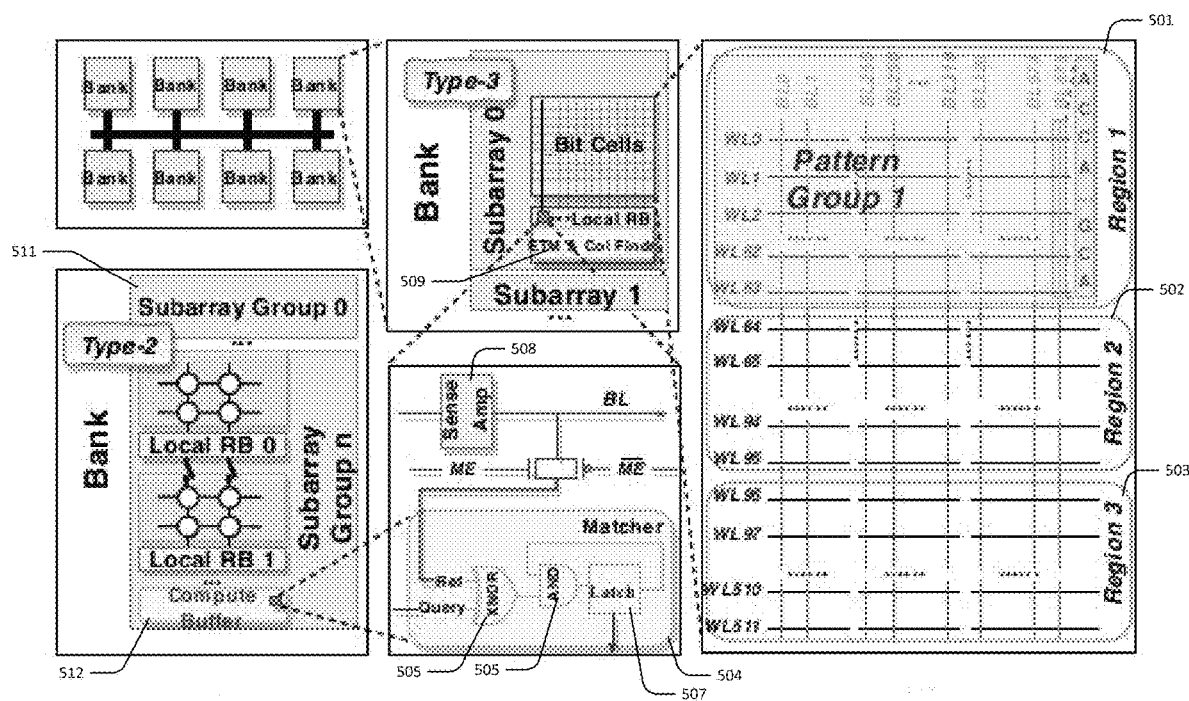
FIG. 5 is a block diagram illustrating sequence matching apparatus according to various embodiments.

FIG. 5 illustrates Type-2 and Type-3. The types differ mainly in the placement of the add-on logic (e.g., matching circuitry) at the bank vs. subarray level, but share the same data mapping scheme. Next, we describe the key components of Sieve and tie them together with a k-mer matching walkthrough.

Data Layout. K-mer patterns are encoded in binary (A: 00, C: 01, G: 10, T: 11) and transposed onto bitlines BL0, . . . , BL575, for column-wise placement, as described in the previous section. Bit cells within each subarray are divided into three regions 501, 502, 503 (shown in FIG. 5). However, we note that no physical modification is made to the bit cells. Region-1 501 stores the interleaved reference and query k-mers. Region-2 502 stores the offsets to the starting address of payloads (one for each reference k-mer), allowing us to precisely locate the payloads. Region-3 503 stores the actual payloads such as taxon labels. Data in Region-2 502 and Region-3 503 is stored in conventional row-major format. The main motivation to co-locate patterns and payloads is to minimize contention and achieve higher levels of parallelism. If patterns are densely packed into several dedicated banks/subarrays, all matching requests will be routed to them, inevitably creating bank access contention and serializing such requests.

Region-1 501 is further broken down into smaller pattern groups and a batch of 64 (different) query k-mers are replicated in each pattern group. This is because the transmission delay of long wires inside DRAM chips prevents us from broadcasting a query bit to all matchers (discussed next) during one DRAM row cycle. All pattern groups in a subarray work in the lockstep manner. The exact size of a pattern group is equivalent to the number of matchers that a query bit can reach in one DRAM row cycle. In this example (a DDR3 Micron 32 M 8 B x4 sg125 DRAM), it happens to be 576 (512 reference k-mers+64 query k-mers). The number of query k-mers per batch is determined by the chip's prefetch size. In this example, a chip with a prefetch size of 8 bytes writes 64 bits with a single command. A chip with smaller (larger) prefetch size has smaller (larger) batch size. After a batch of query k-mers finishes matching in a subarray, they are replaced by a new batch. The total number of write commands needed to replace a batch of 64 k-mers can be computed as (number of pattern groups per subarray)* (k*2).

Matcher. We enhance each sense amplifier 508 in a row buffer with a matcher 504 shown in FIG. 5. The matcher of Type-2 and Type-3 is made of an XNOR gate 505, an AND gate 506, and a one-bit latch 507. The XNOR gate 505 checks if the reference bit and the query bit at the current base are equal. The bit latch 507 stores the result of the XNOR operation, indicating if a reference and a query have been matched exactly up until the current base. The value in each bit latch is set to 1 initially (default to match). The AND gate 506 compares the previous matching result stored in the bit latch with the current result from the XNOR gate 505 and updates the bit latch 507 accordingly, in essence, capturing the running match outcome bit-by-bit. Finally, we allow the matcher to be bypassed or engaged by toggling the Match Enable signal ME/ME.

When a row is opened, both query and reference bits are sent to the sense amplifiers. A subarray controller (sCtrl) then selects which query to process among the 64 queries in the subarray. Each pattern group has a 1-bit shared bus (not shown in the figure) connecting all matchers. The selected query bit is distributed to all matchers in a pattern group through this shared bus.

Figure 7:
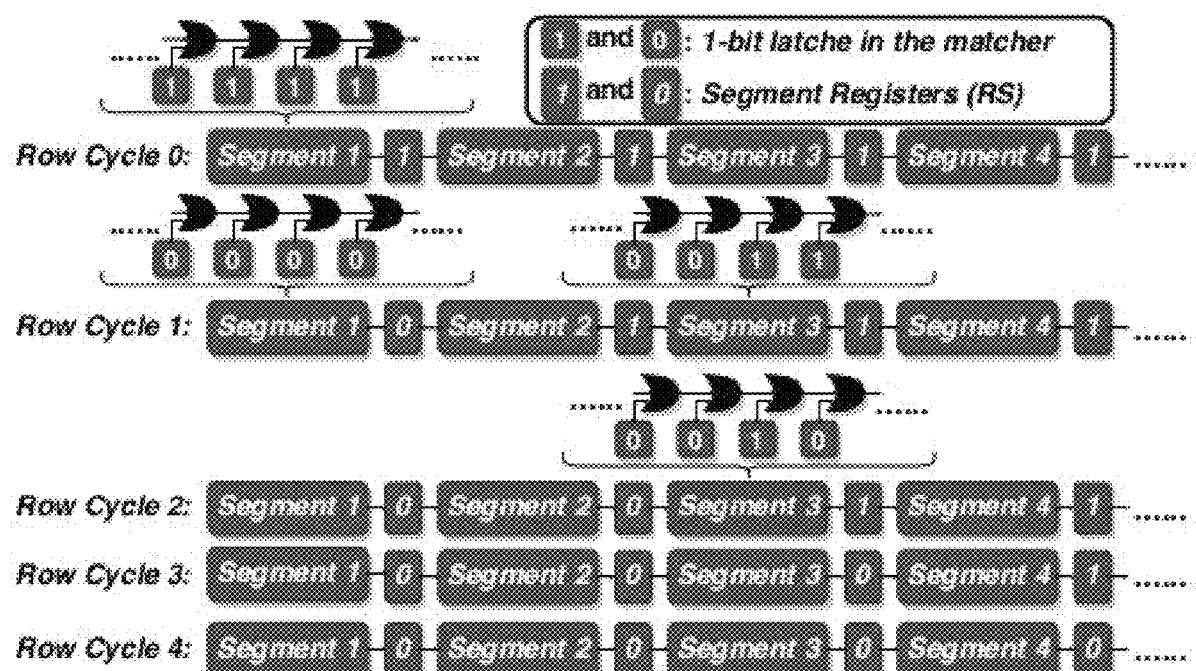
FIGS. 7 and 8 illustrate operations for segmentation and early termination of a matching process according to some embodiments.

Early Termination Module (ETM). The ETM module 509 interrupts further row activation by checking if the entire row of latches is storing zeros. The k-mer matching process continues if at least one latch stores 1. The natural way is to OR the whole row of latches. However, the challenge of this approach is that each OR gate adds to the latency, and during one DRAM row cycle, only a small fraction of result latches can propagate their results through OR gates. We propose a solution that breaks the row of latches into segments and propagates the partial results in a pipelined fashion as shown in FIG. 7. One segment register (SR) is inserted for every 256 latches to implement the pipeline. During one DRAM row cycle, each segment takes the value from the previous SR, ORs it with all its latches, and outputs the value to the next SR. Notice that in FIG. 7, although at row cycle 3, all latches store zeros, the last SR still holds 1. This is an artifact of our pipelined implementation, where an extra cycle is needed to flush the result.

Figure 6:
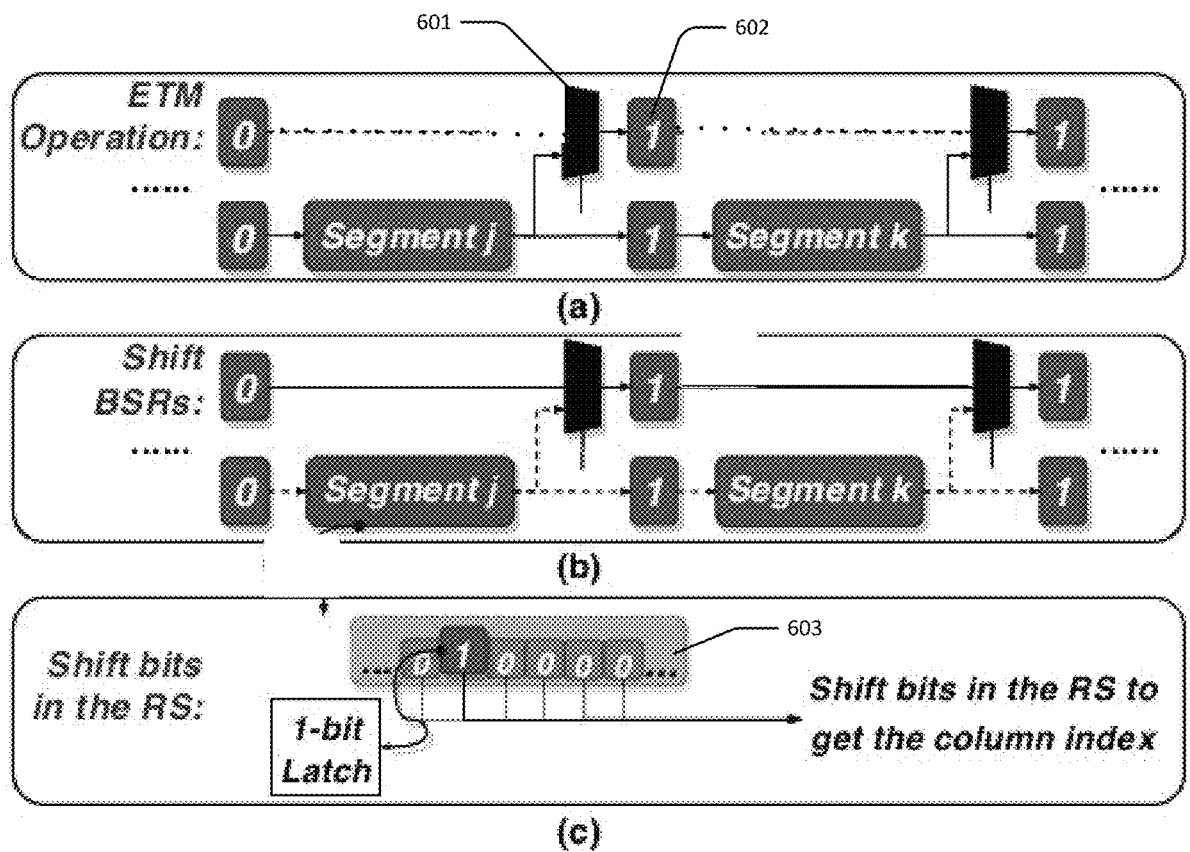
FIG. 6 illustrates a pipelined, two-level shifter solution for a column finder according to some embodiments.

Column Finder (CF). Unless interrupted by the ETM module 509, the row activation continues until all bases of a query are checked. If a query is previously matched to a reference, one and only one latch in a row buffer stores one. The CF 510 identifies the column (bitline) that is connected to that latch. The column numbers are needed to retrieve offsets, and subsequently, payloads. Our solution is to shift a row of latched bits until we find a one. The challenge of this approach is to design a shifter with reasonable hardware cost and latency. In the worst case, where the matched column (reference k-mer) is located at the end of the row, the CF 510 needs to shift an entire row of latched bits. We propose a pipelined, two-level shifter solution for CF 510. FIG. 6 illustrates this idea. The CF 510 circuits are re-purposed mainly from those of the ETM module 509. For each ETM segment, a MUX 601 and a 1-bit Backup Segment Register (BSR) 602 are added. BSRs and SRs maintain the same values and are updated simultaneously during the ETM operation. Zero in a BSR 602 means that its associated segment does not contain a match, and one implies it does. Further, we add another set of bit latches called the Reserved Segment (RS) 603, which includes the same amount of 1-bit latches and OR gates as a segment. We describe the operation of the CF 510 in more detail below.

Figure 8:
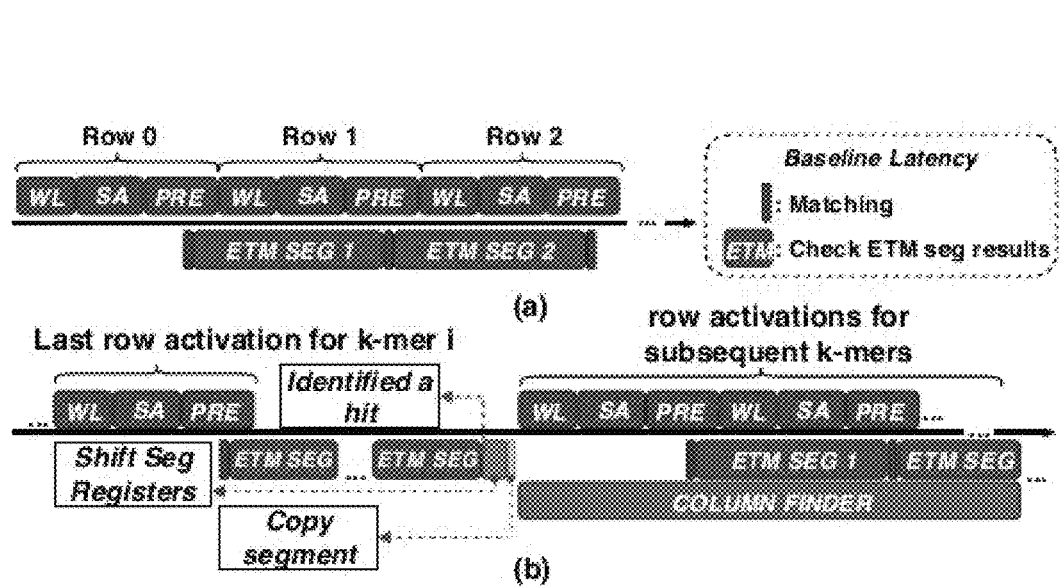

We first shift the BSRs until we find a one, to narrow down the appropriate segment that contains a match (FIG. 6). We then copy this segment over to the Reserved Segment (RS) where the final round of shifting happens. From this point on, all ETM segments are freed to support the pattern matching for the next k-mer, while the CF works in the background to retrieve the column number (see FIG. 8). The shifting of bits in RS is overlapped with the matching of the subsequent k-mer. We point out two details here. First, after the last row activation for a given query k-mer finishes, ETM takes up to 256 DRAM row cycles to flush the pipeline in the worst case, when the one is at the very end. During this time, no new row activation is issued, and the CF operation is stalled until ETM completes. Second, we note that each k-mer hit takes up to 4800 DRAM cycles, while the CF operation takes up to 1032 DRAM cycles in the worst-case scenario. Therefore, we observe no contention at the CF, even when there are two consecutive hits in the same subarray.

Sieve Type-2. While Sieve Type-2 retains most of the high-level design from Type-3 (ETM, data mapping, matching circuits, etc.), it differs in one key aspect—instead of integrating logic to all subarrays at the local row buffer level, logic is added to a subarray group—a subset of adjacent subarrays within a bank (e.g., ½, ¼, ⅛ of subarrays) connected through high bandwidth links (isolation transistors). Each subarray group 511 is equipped with a compute buffer 512, which retains much of the capabilities (k-mer matching, ETM, and column finding) of a local row buffer in Type-3 without its sense amplifiers. Unlike type-3, where k-mer matching is performed locally at each individual subarray, Type-2 processes k-mer matching inside the compute buffer 512 regardless of the target subarray query k-mers get dispatched to. This involves transferring a row of bits across subarrays to reach the compute buffer at the bottom of the subarray group. To enable fast row copy across subarrays, we leverage a previous work LISA for low-cost inter-subarray data movement, albeit adapted to the folded-bitline architecture that Sieve is built upon. We validate the feasibility of our design with the help of a detailed circuit-level SPICE simulation as discussed in Section VI.

Figure 9:
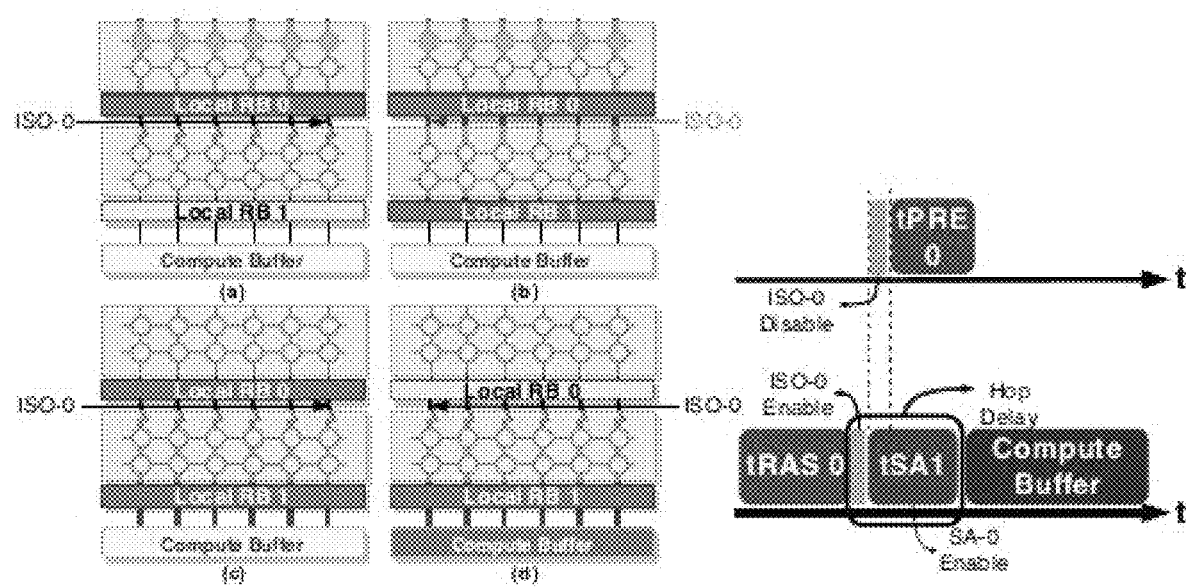
FIG. 9 illustrates a process of transferring a row from the source subarray to its compute buffer according to some embodiments.

FIG. 9 illustrates the process of transferring a row from the source subarray to its compute buffer—(a) the DRAM row in the subarray 0 is activated and the data is latched onto its local sense amplifiers, (b) when the bitlines of subarray 0 are fully driven, the links between the subarray 0 and subarray 1 are enabled. Due to charge sharing between the bitlines of subarrays 0 and 1, the local sense amplifiers in the subarray 1 senses the voltage difference between the bitlines and amplifies it further, as a result of which, (c) local sense amplifiers in both subarrays 0 and 1 start driving their bitlines to the same voltage levels, and finally, (d) when both sets of bitlines in subarrays 0 and 1 reach their fully driven states, the isolation transistors between them are disconnected and the local sense amplifiers in the subarray 0 are precharged. The process is repeated until the data reaches the computed buffer. Note that—(1) only two sets of local sense amplifiers are enabled at any time in a bank, and (2) as validated in our Spice simulation, the latency of activating the subsequent sense amplifiers (tSA in FIG. 9 is much smaller (~8×) than activating the ones of the source subarray (tRAS). The latency for one row to cross a subarray (except for the first one) is referred to as "hop delay" which consists of enabling the isolation transistors (link) and the activation of the sense amplifiers.

K-mer Matching Walkthrough. We use Type-3 as an example to illustrate the k-mer matching process. Once a row is selected for activation, both the query and the reference bits are sent to the local row buffer for comparison using the mechanisms described above.

The ETM checks all segments and propagates the values of Segment Registers (SRs) to determine if a match is found, at which point no further row activations are issued. Once a match is found, the payload associated with that k-mer pattern is retrieved as follows. The CF first determines the segment number by shifting all BSRs. It then gets the column index by shifting all 1-bit latches in that segment until the one is found. The column number is calculated as segment number*(number of columns/segment)+column index and sent to subarray controller to index into the payload address offsets.

Sieve Type-1

Strictly speaking, Sieve Type-1 is not a quintessential in-situ architecture, due to the lack of processing unit embedded in row buffers. However, Type-1 preserves the overall high-level ideas, such as the data layout, ETM, and the matching unit. In addition, Type-1 is the least intrusive implementation of Sieve because it does not change the physical layout of DRAM banks. The bank I/O width is 64 bits, and each row is 8192 bits. Thus, a row is divided into 128 batches. A batch is a set of bits retrieved by a DRAM read burst of a read command Batch size varies depending on the column width, which can be 32, 64, or 128 bits. Next, we introduce each component of Type-1 briefly.

SRAM Buffer (SB). SB stores the match result bits, which are organized in a 2D array. The number of entries is equal to the number of batches, and the entry width is the batch size. Before matching, all batch result bits are preset to one, and the result bits are updated as the matching progresses, again capturing the running match outcome.

Matcher Array (MA). MA consists of 64 matching units. It compares a query bit with the reference bit using an XNOR gate, and updates (writes back) the result bit by ANDing the match result bit stored in SB with the output from XNOR.

Skip Bits Register (SkBR). SkBR is used for ETM. It contains one bit for each batch indicating if we need to process the current batch. All bits in SkBR are preset to one. As the matching progresses, more and more bits in SkBR is set to zero, meaning more and more batches will be skipped. Without SkBR, each row activation is followed by 128 batch comparisons. Since most comparisons result in mismatches, SkBR leads to significant energy and latency reduction.

Start Batch Register (StBR). The motivation for having an StBR is to reduce processing time further. Due to the ETM, Type-1 checks the skip bits one by one to find proper batches to send to the MA. The search time is one DRAM cycle per skip bit. In the worst case where only the last batch is valid, 127 DRAM cycles are wasted to check all the previous skip bits. With the help of the StBR, whose value points to the first batch that needs to be processed, Type-1 can quickly determine the first batch to open.

Column Finder and Payload Retrieval. The control logic first checks the skip bits to locate the batches that contain a one, given the one-to-one mapping between batches and skip bits. A small shifter is applied to get the index of the matched column in the batch. The column number is calculated as (batch index)*(batch size)+(column index), and is then used by the control logic to get offsets and payload.

System Integration

This section provides a discussion on how the different Sieve designs can be integrated into a modem computing system, while maintaining sustainable power delivery and bandwidth. We consider two form factors: (a) Dual-Inline Memory Module (DIMM), and (b) PCIe. While PCIe incurs extra communication overhead due to packet generation, DIMM suffers from limited power supply. A typical DDR4 DIMM provides around 0.37 Watt/GB of power delivery and 25 GB/s of bandwidth, which is sufficient for Type-1. However, Type-2/3 exceeds the power cap of DIMM, thus requiring PCIe integration. To satisfy the bandwidth, Type-2 needs at least PCIe 3.0 with 8 lanes, and Type-3 needs at least PCIe 4.0 with 16 lanes. Note that the DIMM configuration can be used as conventional memory when not being used for Sieve. The accelerator card, in a future CXL bus, can also serve as (slower) memory.

We use a 32 GB Type-2 Sieve to illustrate how Sieve communicates with the host using a PCIe interconnect. Unlike Type-1, which communicates with the host on individual k-mer requests, Type-2/3 uses a packet-based protocol that delivers hundreds of k-mer requests per PCIe packet. A PCIe Type-2/3 accelerator maintains two queues for accepting (PCIe Input Queue) and returning (PCIe Out Queue) PCIe packets, and a response ready queue (RRQ) to hold serviced k-mer requests. The CPU scans the query sequences to generate k-mers, and for each k-mer, it makes a 12-byte request that contains the pattern, sequence ID, destination subarray ID, and other header information. Each PCIe packet contains 340 requests, assuming 4 KB PCIe packet payload size. Each Sieve bank buffers 64 requests. To fully saturate the capacity of a 32 GB Sieve, the depth of the PCIe queue is set to 24 (24 PCIe packets*340 requests/packet 16 ranks*8 banks/rank*64 requests/bank). As the capacity of Sieve grows, deeper queues can be useful due to the potential increase in the number of banks, allowing more requests to be handled simultaneously. Sieve removes the PCIe packets from PCIe Input Queue, unpacks them, and distributes requests to the target banks. A finished request gets moved to the RRQ. Once the RRQ is full, a batch of PCIe packets is moved to the PCIe Out Queue. Sieve sends an interrupt to the CPU if the packets are waiting in the PCIe Out Queue or if there are empty slots in the PCIe Input Queue.

The entire space of Sieve is memory-mapped to host as a noncacheable memory region, avoiding virtual memory translation and cache coherence management. Regardless of configuration (DIMM or PCIe), a program interacts with the Sieve device through the Sieve API, which supports calls to transpose a conventional database into the format needed for column-wise access (this can be stored for later use and is thus a one-time cost); load a database into the Sieve device; and make k-mer queries. The API implementation requires a user-level library and an associated kernel module or driver to interface to the Sieve hardware. The exact API and implementation are a subject to future work. K-mer databases are relatively stable over time, so once a database is loaded into the Sieve device, it can be used for long periods of time, until the user wishes to change a database. The same databases are often standard within the genomics community, so even in the cloud deployment, discussed below, high reuse can be expected. In either case, the cost of loading the database is amortized over an extended period of use.

K-Mer to Subarray Mapping

One of the major strengths of the Sieve architecture is its ability to effectively exploit bank-level and subarray-level parallelism. However, without an appropriate mapping scheme, each query needs to be broadcast across all regions of the accelerator. A naïve mapping scheme would involve looking up an index table that maps queries to banks (Type-1) or subarrays (Type-2 and Type-3). We note that such a scheme would quickly stop scaling, as the size of such an index table increases exponentially with the length of a k-mer. As an example, consider a typical k-mer length of 31, in which case, such an index table would have to be provisioned with $4^{31}$ entries, taking up hundreds of gigabytes of space that needs to be accessed frequently, creating a significant performance bottleneck. To this end, we design an efficient and a scalable indexing scheme, wherein the size of the index table scales linearly with the main memory capacity rather than the length of a k-mer. More specifically, the reference k-mers in each subarray are sorted alphanumerically from left to right, and then each entry in our index table maintains an 8-byte subarray ID along with the integer values of the first and the last k-mers at the respective subarray (identified by the index). Upon receiving a matching request, Sieve first converts the query k-mer to its integer representation, and consults the index table to select the bank/subarray that potentially contains a match. For a 32 GB Sieve built from Micron DDR4 chips (DDR4 4 Gb 8 B x16), the index table takes 2 KB (128 entries) for Type-1, and 128 KB for Type-2/3 (8192 entries). While Type-2/3 exploit different levels of parallelism, they share the same indexing scheme, i.e., if Type-2 only provides the bank address to our indexing scheme, a query needs to be checked against every subarray in that bank. The size of the index table stays well under 2 MB even for Sieve Type-2/3 with 500 GB of capacity, which is reasonable for a dedicated bioinformatics workstation that is typically provisioned with that level of memory resources.

E. Sieve: Putting it All Together

In this section, we describe how K-mer matching requests arrive and exit Sieve. For Type-2/3, the host (CPU) reads the input query sequences and extracts k-mer patterns. For each k-mer, the k-mer to subarray index table is consulted to locate the destination subarray, and a k-mer request is made, as described in Section IV-C. A number of k-mer requests that need to be sent to the same subarray is grouped into one "batch". The exact number of k-mer requests per batch is equal to the number of query k-mers in a pattern group (64 in our example). These query batches are placed in a buffer, ready to be transferred to the PCIe device buffer by DMA. PCIe bundles several such batches into one PCIe packet (also described in Section IV-C), and ships them to the Sieve device. Sieve dispatches each batch of query k-mers to the destination subarray, and replaces an already processed query k-mer batch with a new (to-be-processed) batch, as described in Section IV-A.

Figure 2:
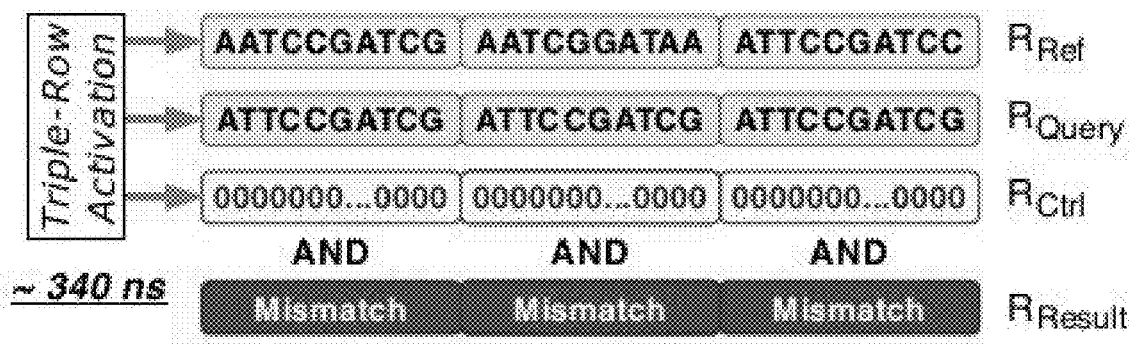
FIG. 2 is a chart illustrating a conventional sequence matching process.

Individual k-mer requests in the same batch potentially complete at different times as (1) they get issued out-of-order (as soon as their bank/subarray becomes available), and (2) each request may involve checking a different number of rows. Thus, response packets may arrive out-of-order at the host, where their sequence IDs and payloads are examined, as part of a post-processing step. Upon the completion of all k-mer requests for a given sequence, the accumulated payloads can be fed into an appropriate classification step, as illustrated in FIG. 2. We note that there is no additional reordering step required at the host end as the accumulated payloads are typically used to build a histogram of taxons for a given DNA sequence.

Discussion

Deployment Model and Cost Analysis. Sieve provides orders of magnitude speedup and energy reduction over CPUs and GPUs for k-mer matching tasks deployed in many critical domains, including disease surveillance, cancer diagnostics, precision medicine, and public health. Traditionally, end-users are required to purchase and integrate such accelerators into their on-site infrastructures to fully reap the benefits they provide. However, in many instances, this deployment model is economically infeasible for both semiconductor manufacturers and consumers. For example, smaller bioinformatics labs with limited financial support typically avoid paying high premiums for dedicated in-house accelerator boards, because the performance gains may not eventually translate to sufficient savings over the lifetime of the accelerators.

Note that genomic analysis tasks are typically composed of discrete stages, each of which likely has optimal accelerator designs. Acquiring accelerators for all stages in an analysis pipeline maximizes performance, but causes significant financial burdens for small labs. Therefore, we envision Sieve to be deployed in the cloud among a sea of other genomics accelerators to fulfill the need for faster genome analysis, amortizing the Non-Recurring Engineering (NRE) cost and the Total Cost of Ownership (TCO) of developing and maintaining Sieve (and other bioinformatics accelerators) among the entire community of users.

Since data centers comprised of proprietary accelerators (ASIC-based or FPGA-based) for non-general-purpose computing such as Bitcoin mining, high-frequency trading, and web search acceleration are common nowadays, and genomic analysis is growing rapidly, often with high performance sensitivity (e.g., research on COVID-19), it seems reasonable to posit interest in cloud support for faster k-mer matching. In fact, a recent proposal calls for the deployment of FPGA-based accelerators in the cloud context to solve the INDEL realignment bottleneck in the DNA alignment refinement stage, showing excellent cost efficiency over CPU and GPU clouds. Due to the extensive presence of k-mer matching in bioinformatics, Sieve is likely to be a staple residing in genomic cloud environments to support many high-volume, planet-scale genomics analysis tasks.

Cloud providers make profits switching from conventional clouds (CPU or GPU based) to clouds with novel accelerators when two conditions are met: (1) the TCO per operations per second (TCO/ops/s) benefit of the accelerator cloud >2×, (2) and TCO of the current cloud >2×NRE of a new cloud. The accurate modeling of the NRE and the TCO for developing and deploying Sieve in clouds is out of the scope of this paper, because it requires knowledge on cloud environments' server design (heat sink, power delivery, and PCB layout), warehouse-level parameters (land, interests, and electricity), labor, IP costs, mask costs, characteristics of other accelerators coexisting in the clouds, and the size of the customer base. We provide some data points for a coarse-grained analysis. First, we show that condition two is satisfied. If the energy efficiency (Watt/op/s) and cost-performance (performance per $ of hardware) is 2× better than the current solution, the TCO/ops/s will have twice the improvement. Sieve achieves orders of magnitude improvement over CPUs and GPUs in terms of Watt/op/s. Using DRISA as a proxy, which has 6× cost efficiency over GPUs because DRAM-based accelerators usually have a smaller number of metal layers and external pins, Sieve clears the cost-performance bar too. For condition one, we use a public-available TCO calculator, which considers the floor space (7,000 sq.ft. to 21,000 sq.ft.), base rent ($150 to $210), utility power (1 MW to 3 MW), and the life-span of a datacenter (3 years), to get a range of TCOs for maintaining a datacenter across the country (8.7 to 34 million dollars). This TCO model excludes the cost of computing equipment. We use the NRE of video transcoding ASIC design as a surrogate to estimate the NRE of Sieve, since both workloads are memory intensive, and their hardware resources are primarily devoted to DRAM. Considering all facets that contribute to the NRE (labor, IP licensing, packaging, mask, etc.), and assuming the technology nodes are between 40 nm to 65 nm, we roughly estimate the NRE of Sieve to be around 3 to 4 million dollars, which is significantly lower than TCO of current clouds. Thus deploying Sieve in the cloud is likely to benefit cloud providers as well.

ECC. K-mer matching is already highly error-tolerant; the rate of errors in sequencing DNA is of order of 10e-3, much higher than DRAM error rate. Prior work has shown that the average (median) error rate of DRAM per month per server is 497. Therefore, per 4 GB DRAM, the error rate/month, is order 10e-6, which is negligible by comparison. Furthermore, failures from the memory controller and memory channel have been shown to cause the majority (85%) of DRAM errors. This means that the order of error rate of Type-2 and Type-3 should be much lower than 10e-6. As future work, we plan to explore adding parity support within each subarray.

Methodology experimental methodology, including application kernels, tools, baselines, and modeling assumptions.

Workloads. For the CPU baseline, we extract k-mer matching kernels from the state-of-the-art metagenomics tools, Kraken2 and CLARK (hashing-based). Recent studies indicate that they are highly comparable and consistently rank at the top in terms of sequence classification accuracy, sensitivity, and speed. For the GPU baseline, we use kernels from cuCLARK, which is the GPU-based CLARK. For the FPGA baseline, we choose the Mercury System, which accelerates the BLAST word matching stage (implemented as hash table lookup), a process highly comparable to k-mer matching.

Input Data. We use real-world reference datasets from MiniKraken 4 GB, MiniKraken 8 GB, NCBI Bacteria (2785 full bacterial genomes), and a whole human genome GRCh37 (3 billion base pairs). Query sequences are summarized in Table I.

TABLE I

Query Sequence Summary

| Query Sequence File | Number of Sequences | Sequence Length |
|---|---|---|
| HiSeq Accuracy.fa (HA) | 10000 sequences | 92 base pairs |
| MiSeq Accuracy.fa (MA) | 10000 sequences | 157 base pairs |
| simBA5 Accuracy.fa (SA) | 10000 sequences | 100 base pairs |
| HiSeq Timing.fa (HT) | 100000000 sequences | 92 base pairs |
| MiSeq Timing.fa (MT) | 100000000 sequences | 157 base pairs |
| simBA5 Timing.fa (ST) | 100000000 sequences | 100 base pairs |

Baseline Performance Modeling. Our workstation configurations are reported in Table II.

TABLE II

Workstation Configuration

| | |
|---|---|
| CPU Model | Intel(R) Xeon(R) E5-2658 v4 |
| Core/Thread/Frequency Range | 14/24/2.30-2.80 (GHz) |
| L1 (KB)/L2 (KB)/L3 (MB) Cache | 32/256/35 |
| Main Memory | DDR4-2133 MHz |
| Memory Organization | 32 GB/2 Channels/2 Ranks |
| GPU Model | Pascal NVIDIA Titan X |

To capture the baseline performance, we use default application settings and report the best results of three consecutive runs, similar to the CuCLARK methodology. The FPGA baseline is estimated by aggressively scaling up performance from the original Mercury System document using parameters of the Xilinx Virtex-4QV FX. The GPU and FPGA baselines are idealized because (1) the energy and latency of data transfer from host to accelerator boards are not included, and (2) the on-board memory is always large enough to avoid running each query multiple times. The baseline DRAM energy consumption is estimated by feeding memory traces associated with k-mer matching functions using a custom Pin tool from to DRAMSim2, which is configured to match the same setting as our workstation. We use a similar methodology described in to estimate CPU and GPU energy. The CPU energy is measured using the Intel PMC-power tool, then scaled down by 30% to exclude the interference from other parts of the system. The GPU energy is measured using NVIDIA Visual Profiler and scaled down by 50% to exclude the energy spent on cooling and other operations. The Mercury System did not report energy data.

Circuit-level SPICE Validation. Of all the Sieve components, only the Matchers are in direct contact with the sense amplifiers' BLs. In the presence of the Matcher circuit, the load capacitance on the BL is increased. We use SPICE simulations to confirm that Sieve works reliably. The sense amplifier and matcher circuits are implemented using 45 nm PTM transistor models. Because of the relatively small input capacitance of the matcher circuit (~0.2 pf), in comparison with the BL capacitance (~22 pf), the matcher has a negligible effect on the regular operation of the sense amplifiers. We find that, after the row activation and when the BL voltage is at a safe level to read, the matcher is enabled at 40 ns, and the result of the matcher is ready after less than 1 ns. In our experiments, we sweep through different values of the initial charge of the cell to consider the effect of DRAM cell charge variations. In all cases, we find that the matcher and the link between two subarrays do not cause any bit flip or distortion.

Energy, Area, and Latency Modeling. We estimate the power and latency overhead of each Sieve component using FreePDK45. Further, we use OpenRAM to model and synthesize the SRAM buffer in Sieve Type-1. We use scaling factors from Stillmaker, et al. to scale down the results to the 22 nm technology node, and use the planar DRAM area model proposed by Park, et al. to estimate the area overhead.

Sieve Performance Modeling. We assume a pipelined implementation of Sieve where the host (CPU) performs the pre-processing (k-mer generation, driver invocation, and PCIe transfer) and post-processing (accumulation of response payloads for genome sequence classification) steps, while the Sieve device is responsible for the actual k-mer matching. Our analysis confirms that the latency of this pipelined design is limited by k-mer processing on Sieve. In particular, the k-mer matching on our Sieve designs is either comparable to (Sieve Type-3) or slower than (Sieve Types-1/2) both pre- and post-processing steps on the CPU, as a result of which the CPU is always able to blast k-mer requests to the Sieve device and keep it busy.

We model the pre- and post-processing steps using the baseline CPU described in Table II. We treat the classification step as a separate pipeline by itself as (1) the algorithm differs for each application, and (2) it is independent of k-mer matching, which is the primary focus of this work. Thus, we forgo modeling the effort required for genome classification, post k-mer processing. For modeling the k-mer matching itself, we use a trace-driven, in-house simulator with a custom DRAMSim2-based front-end. The simulator also models PCIe communication overhead, using standard PCIe parameters. We use a Micron DDR4 chip (DDR4 4 Gb 8 B x16) as the building blocks for Sieve. The DRAM parameters are extracted from the same datasheet and modified to account for the estimated latency and energy overhead of matchers, ETM, CF, and segment finder.

VII. EXPERIMENTAL RESULTS

Energy, Latency, and Area Estimation

Energy Evaluation. Table III summarizes the dynamic energy and static power of each Sieve component.

TABLE III

Sieve Components Energy and Latency Analysis

| Component | Dynamic Energy (pJ) | Static Power (uW) | Latency (ns) |
|---|---|---|---|
| (T1) 64-bit MA | 0.867 | 1.4592 | 0.353 |
| (T1) QR, SkBR, StBR | 1.92 | 5.28 | 0.154 |
| (T1) SRAM Buffer | 5.12 | 4.445 | 0.177 |
| (T2/3) 8192-bit MA | 181.683 | 0.289 | 0.535 |
| (T2/3) ETM Segment | 73.5 | 56.185 | 43.653 |
| (T2/3) Segment Finder | 2.44 | 0.294 | 0.362 |
| (T2/3) Column Finder | 20.69 | 28.16 | 0.152 |

Types-3 incur additional power consumption for each DRAM row activation. However, compared to a regular DRAM organization, they consume only 6% more energy for each row activation, because the minimalistic nature of the actual logic we integrate into the row buffer. More specifically, the area and the load of these transistors is considerably small compared to the sense amplifier and the bitline drivers. We further break down this energy overhead to understand the effect of the different Sieve components. We find that the Matcher Array (MA) and the ETM dominate the energy consumption, capturing 78.9% and 15.8% of the 6% energy overhead incurred by Sieve, with the energy spent by the Segment Finder and the CF being negligible (less than 5% of the total energy overhead). Type-1 adds no overhead on top of the regular DRAM row activation because no modification is made to the row buffer, and it is less energy-intensive than Type-2/3 overall.

Latency Evaluation. Table III shows the latency of each Sieve component. For Type-1, we reckon that (1) accessing the SRAM buffer and the Query Register can be overlapped entirely with a column read command (~15 ns) that retrieves a batch of reference bits, and (2) although the pattern matching and register checking are on the critical path, collectively, they add a negligible amount of overhead (~0.5 ns) to the DRAM row cycle (~50 ns). For Type-2/3, each ETM segment (256 OR gates) meets the timing requirement of completing its operation within one DRAM row cycle. Further, since the segment and column finders are essentially composed of simple shifters, their latency of operation is well within one DRAM cycle (0.625 ns).

Area Evaluation. To estimate area the overhead of Sieve, we use the model proposed by Park et al. We adopt the DRAM sense amplifier layout described by Song, et al. for a conventional 6F2 DRAM layout. The short side and long side of the sense amplifier are 6F and 90F, respectively. In Sieve Type-2/3, for the accommodation of the matcher, ETM, segment, and column finder circuits in the local row buffer, we add 340 F in total on the long side of the local sense amplifiers. For Sieve Type-2, an extra 60 F in long side is added to each sense amplifier for considering the area overhead of the links between the subarrays.

The area overheads for Sieve Type-2 designs with 1, 64, and 128 computer buffers (CB) are 1.03%, 6.3% and 10.75%, respectively, for a DRAM chip with eight banks. In Sieve Type-3, each local sense amplifier is enhanced with k-mer matching logic, and for enabling subarray parallelism a row-address latch is added to each subarray, resulting in 10.90% area overhead. For Sieve Type-1, all components are added to the center strip of our DRAM model. In addition to the matching logic in each bank, we add an SRAM buffer of size of 8 Kbits (128 Rows×64 Bits) to each bank within the DRAM chip. The SRAM buffers and the matching circuit increase the chip area by 2.4% and 0.08%, individually. Note that these figures do not expose the additional area that is required for routing logic between the global sense-amplifiers, SRAM buffers, and matching logic.

Kernel Performance Improvement

K-mer matching Bake-off. We report in Table IV the peak throughput (bases per second) and peak throughput per watt for each platform, across all the benchmarks.

TABLE IV

Peak Throughput and Peak Throughput/Watt

| Architectures | Peak Throughput | Peak Throughput/W |
|---|---|---|
| CPU (28 threads) | $4.01 * 10^7$ bases/s | $1.26 * 10^6$ bases/s/w |
| GPU | $7.85 * 10^7$ bases/s | $1.5 * 10^6$ bases/s/w |
| FPGA | $5.5 * 10^9$ bases/s | NA |
| Sieve (T1) | $4.42 * 10^7$ bases/s | $1.26 * 10^7$ bases/s/w |
| Sieve (T2.1CB) | $5.11 * 10^7$ bases/s | $1.23 * 10^6$ bases/s/w |
| Sieve (T2.16CB) | $3.09 * 10^7$ bases/s | $1.76 * 10^6$ bases/s/w |
| Sieve (T2.128CB) | $4.83 * 10^8$ bases/s | $4.68 * 10^7$ bases/s/w |
| Sieve (T3.2LR) | $1.24 * 10^{10}$ bases/s | $1.16 * 10^9$ bases/s/w |
| Sieve (T3.4LR) | $2.45 * 10^{10}$ bases/s | $1.16 * 10^9$ bases/s/w |
| Sieve (T3.8LR) | $5.08 * 10^{10}$ bases/s | $1.696 * 10^9$ bases/s/w |

For Sieve Type-1/2/3, we fix their memory capacity to 32 GB to match that of our workstation setting. For Type-2, 1CB/8CB/64CB represents the 1/8/64 compute buffers per bank. We choose 1/8/64 because they are the two extremes and a mid point for Type-2 design. For Type-3, 2SA/4SA/8SA stands for 2/4/8 concurrently working local row buffers (subarrays) per bank.

There are seven major takeaways from this experiment. First, the CPU baseline is the slowest architecture for k-mer matching, due to its highly memory-bound nature. Second, Sieve Type-1 (32 GB) is about 1.77× slower, but 8.4× more energy efficient than the GPU baseline. However, note that the performance of Sieve scales linearly with memory capacity, and therefore, the Type-1 architecture is expected to provide a higher peak throughput than the GPU baseline as the memory capacity increases. Third, while Type-2 with one compute buffer per bank has slightly better throughput than Type-1, which also has one k-mer matching unit per bank, Type-1 is 10× more energy efficient. The inter-subarray data movement in Type-2 accounts for a significant portion of its overall power consumption. Each activated row has to be amplified by a series of local row buffers (hops) along the path to its compute buffer, where k-mer matching happens. Fourth, the throughput and the energy efficiency of Type-2 increase as the number of compute buffers per bank increases. This is because the number of hops per row activation is reduced with more compute buffers. Fifth, the k-mer matching throughput of the FPGA baseline outperforms Type-2, suggesting an FPGA-based alternative for a k-mer matching accelerator. We suspect that this is because an FPGA chip can interface independently to each bank of DRAM, and the FPGA implementation has a higher clock frequency than in a PIM solution, which uses a slower DRAM process. However, we also note that this number is hard to scale, because once the dataset exceeds the on-board memory capacity, each query needs to be processed multiple times, which decreases the throughput, or multiple FPGA boards need to be deployed, which decreases the energy efficiency. This is highly likely, since a high-end FPGA such as Intel Agilex features only 16 GB memory, while a single human genome stored as unique 11-mers consumes 20 GB of memory. Sixth, Type-3 architectures provide the best performance per Watt, clearly highlighting the efficiency of an in-situ approach. Finally, the subarray-level parallelism exploited in the Type-3 architecture provides significant boost in throughput and efficiency.

Comparison Against Row-major In-Situ Accelerators. To compare Sieve against a multi-row activation and row-wise data mapping-based in-situ design, we first simulate an ideal row-major baseline which mimics prior proposals, and measure its speedup over the CPU baseline. We also implement a version of sieve without ETM (Col-major). We make the following assumptions for the Row-major and Col-major baselines. First, their latency for locating and transferring payloads is assumed to be similar to that of Sieve. Second, both architectures are configured to be the same capacity (32 GB) with the same subarray-level parallelism (8 concurrently working subarrays). Third, they share the same indexing scheme.

Figure 10:
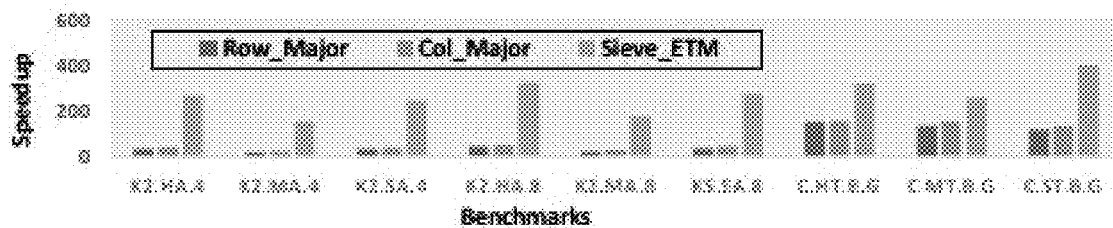
FIG. 10 illustrates a speedup comparison of embodiments to an ideal row-major baseline for an in-situ accelerator.

FIG. 10 shows the results from this experiment. We draw two major conclusions. First, row-major performance is similar to that of the column-major without ETM (slightly worse), but for different reasons. Column-major must activate all the rows that store k-mer data (64 rows if k=32). Row-major stops when it finds a hit, but requires ~10× more writes to set up the comparison as each query k-mer must be replicated across the length of the row. Second, the column-major approach used in Sieve allows it to benefit from our ETM strategy (that provides an additional speedup of 5.2× to 7.2×), in contrast to a row-major design that lacks such an opportunity. We conclude that the chief contribution of column-major layout is therefore 1) in enabling ETM and 2) in amortizing the setup cost across a pattern group of 64 writes. The row-major design performs slightly worse than Sieve Type-3 without ETM. This is because, in the event of a k-mer mismatch, both designs open roughly the same number of rows (62 rows for k=31, and each row has 8192 bits), but the row-major design stops when it finds a hit. We note that, from our evaluation, real sequence datasets are typically characterized by low k-mer hit rates (around 1%), thus favoring Sieve designs.

Figure 11:
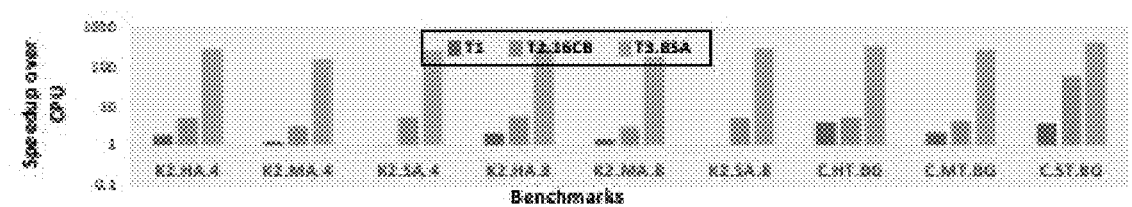
FIGS. 11 and 12 show estimated speedup and energy savings of various embodiments over CPU baselines.
Figure 12:
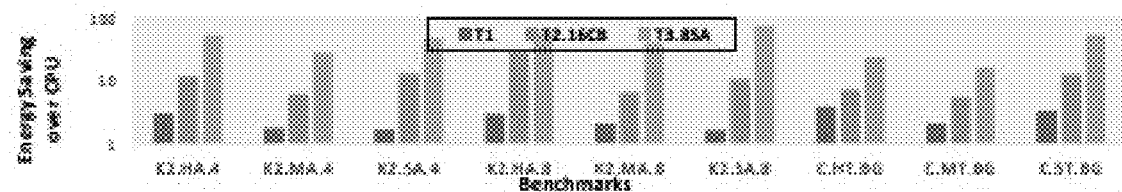

Improvement Over CPU. FIGS. 11 and 12 show the average speedup and energy savings of various Sieve configurations over the CPU baselines. In this experiment, we constrain the memory capacity of all designs to 32 GB. For Type-2, we consider all possible numbers of compute buffers per bank and select the midpoint of 16 (T2.16CB). We present the performance of other Type-2 configurations Section VII-B. For Type-3, we choose the best performer which supports 8 concurrently working subarrays (T3.8SA). We make three major conclusions. While clearly more energy-efficient, Type-1 offers limited speedup (1.01× to 3.8×) for 8 out of 9 benchmarks, showing that for many workloads, there is significant additional performance potential that can be tapped via an in-situ approach. However, we also point out that Type-1 is likely to outperform CPU/GPU as its memory capacity grows (more banks thus more parallelism and bandwidth), while the similar memory-capacity-proportional performance scaling is hard to achieve in a non-PIM traditional architecture. Second, the Type-3 designs offer a speedup and an energy savings of as much as 404.48× and 55.89× respectively, over the CPU baseline. Note that this is in comparison to a Type-2 design that offers a speedup of 55.49× and an energy reduction of 28.11× over the CPU baseline, clearly showcasing the substantial benefits that can be realized by exploiting finer-grained parallelism at the subarray-level. Third, we find that Sieve is sensitive to the characteristics of the application. For example, the C.MT.BG benchmark perform worse than C.ST.BG benchmark as the number of k-mer matches for C.MT.BG is 3.28× higher than C.ST.BG benchmark, resulting in more row activations, increasing the overall query turnaround time and energy consumption. Furthermore, recall that our early termination mechanism interrupts row activations as soon as we detect a mismatch, significantly minimizing the overall turnaround time and energy consumption, for workloads with fewer k-mer matches. In the next subsection, we analyze Sieve's performance in the worst case where every query k-mer is a hit to ensure the robustness of our design.

Figure 13:
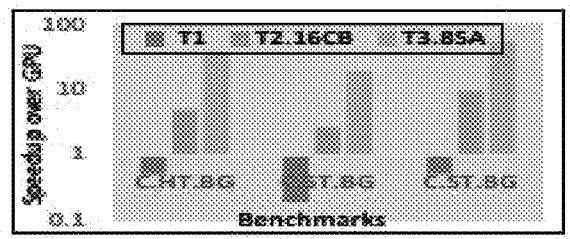
FIGS. 13 and 14 show estimated speedup and energy savings of various embodiments over GPU baselines.
Figure 14:
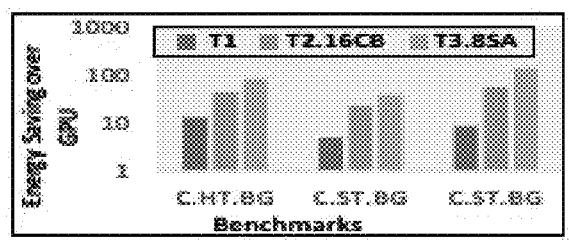

Improvement Over GPU. FIGS. 13 and 14 show the speedup and energy savings of various Sieve designs (32 GB) over the GPU baselines. We draw several major conclusions. First, the Type-1 is 3× to 5× slower than the GPU but more energy efficient, and Type-2 is only modestly faster (2.59× to 9.43×). However, as the memory capacity of Sieve and dataset size increase, Type-1/2 are likely to outperform the GPU soon, because all reference datasets can fit onto Sieve, avoiding the repetitive data transfer from host memory to GPU board. Second, Type-3 dramatically outperforms the GPU, because it leverages subarray-level parallelism. Type-3 offers speeds ranging from 33.13× to 55.0× and energy savings of 83.77× to 141.15×.

Effect of Increased DRAM Bandwidth. In our experiments, we find that the CPU baseline is unlikely to achieve speedup proportional to increasing memory bandwidth, because k-mer matching is not bottlenecked by bandwidth. While memory intensive (high percentage of loads in the ROB), the memory bandwidth is underutilized because each MSHR is unable to serve multiple loads and the available MSHRs are quickly depleted, which stalls subsequent loads in the ROB from being issued, preventing the bandwidth from being fully saturated. To illustrate, consider the microbenchmark, rand ind from Hopscotch that randomly reads values from a large dataset (similar to the random access pattern of k-mer matching) only utilizes 13.6% of the available memory bandwidth on our CPU baseline workstation that features a Broadwell processor. We note that rand ind essentially approximates an upper bound of k-mer matching bandwidth consumption because it reads data into registers without doing any computation (fit as many loads into the ROB as possible) and without any dependency among loads. Further, rand ind has been evaluated on various workstation configurations (2-6 channels, DDR4-2666 to DDR4-3200, and 19-19-19 to 14-14-14), with minimal variations observed in the overall bandwidth.

Even if we overprovision those Broadwell cores with enough MSHRs to sustain all outstanding memory accesses, and all loads are served concurrently with a memory latency of 40 ns, to reach the same level of throughput as Sieve Type-3, the workstation has to be equipped with over 215 such cores, not only resulting in a substantial increase in power consumption (translating into high recurring expenses such as cooling costs), but a considerable wastage in DRAM bandwidth as only a small portion of the retrieved cache line is useful.

Further, we find that the cuCLARK application implements a number of optimizations to improve the performance of our GPU baseline. For example, to minimize the chance of thread divergence, cuCLARK uses one thread block for each sequence, and each thread is responsible for processing one k-mer at a time. We observe several GPU-based BLAST tools which contain a similar dominant stage as k-mer matching achieving the same degree of acceleration (2-5×) over a CPU-based implementation. We suspect that GPUs are constrained by similar bottlenecks as CPUs, although we have not yet pinpointed the exact set of microarchitectural structures. We further note that our FPGA baseline is ideal in that it assumes unlimited bandwidth (zero data transfer cost) and memory capacity (the entire working set fits in the on-board memory, avoiding database swap).

Sensitivity Analysis

Figure 15:
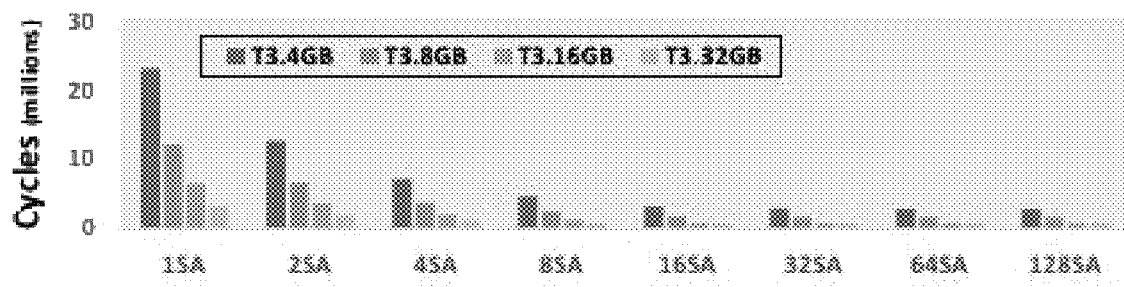
FIGS. 15 and 16 compare various embodiments at different memory capacities and number of subarrays per bank.
Figure 16:
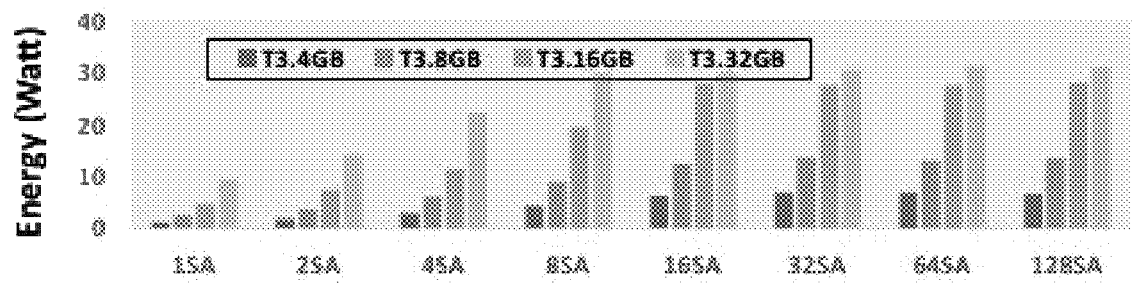

Number of Subarrays per Bank. We next analyze the impact of subarray-level parallelism on performance and energy by comparing various Type-3 design configurations (see FIGS. 15-16) at different memory capacities and number of subarrays per bank. The results are averaged across all benchmarks Supporting all subarrays performing k-mer matching simultaneously without increasing the area overhead significantly is unrealistic in current gen DRAM due to the power delivery. For this experiment, we assume this is not an issue. We make two observations. First, Sieve's k-mer matching throughput can be almost doubled by having twice the amount of concurrently working subarrays, but the speedup plateaus after eight subarrays. The marginal benefit ends at eight arrays/banks because most concurrent bank access conflicts can be resolved by a small number of subarrays. Second, moving from 8 subarrays/bank to 16 subarrays/bank provides little speedup for 4 GB, 8 GB, and 16 GB Type-3 Sieve, but the energy consumption increases dramatically. Greater subarray-level parallelism often draw more power as the number of active logic components is higher. Thus we do not recommend enabling more than eight concurrently working subarrays per bank for Type-3.

Figure 17:
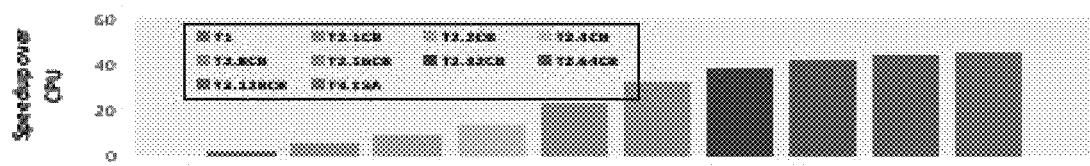
FIGS. 17-19 illustrate effects of varying a number of compute buffers according to some embodiments.
Figure 18:
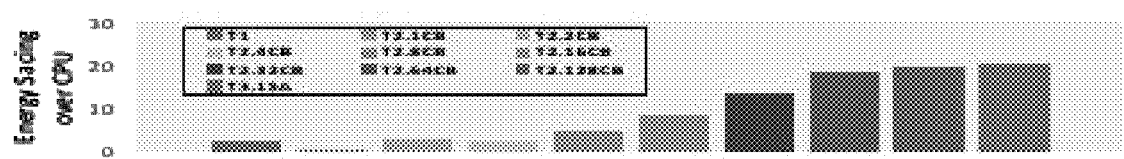
Figure 19:
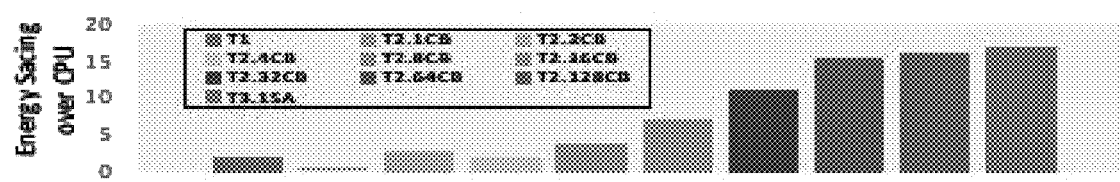

Number of Compute Buffers. We next explore the performance-area tradeoff of our Sieve Type-2 designs, by varying the number of compute buffers (shown in FIGS. 17-19). For reference, we include Type-1 (the left-most bar T1) and Type-3 (the right-most bar T3.1SA) designs without subarray-level parallelism. The middle eight bars represent Type-2 with 1-128 compute buffers per bank. We make the following major observations. First, Type-2 with one compute buffer is faster than Type-1 (1.39× to 1.94×) but not by a large margin. For each row activation, in the worst case, Type-1 has to burst read 128 batches to the matchers, which is similar to T2.1CB where the opened row needs to "hop" across 128 subarrays to reach the compute buffer. Since the hop delay (        ) is faster than a burst latency (tCCD:         ), and both design are equipped with some forms of ETM, T2.1CB is likely to spend less time on data movement than Type-1 in the average case. However, the chain activation of sense amplifiers in Type-2, which relays the row to the compute buffer, consumes significant amount of energy, making Type-2 with sparse compute buffers less energy efficient. Second, generally speaking, increasing the number of compute buffers per bank also increases the speed and energy efficiency of Type-2. As we have explained previously, adding more compute buffers reduces the activation of sense amplifiers, which in turn reduces the delay and energy consumption. Third, the area overhead scales with the number of computer buffers per bank. Finally, the speedup and energy reduction of T2.128CB slightly trails behind those of T3.1SA, because T2.128CB still requires one hop per row activation. However, Type-3 also has a higher area overhead than T2.128CB for enabling subarray-level parallelism.

ETM. To simulate the adversarial case where every query k-mer has a match, we turn ETM off in Type-2/3 (vary the memory capacity), and measure the speedup and energy reduction over CPU baselines (averaged across all benchmarks). While significantly slower and less energy efficient, Type-2 and Type-3 without ETM are still 1.34× to 155.37× faster and 4.15× to 36.17× more energy efficient than CPU, owing to the substantial parallelism and data movement reduction of the in-situ approach. Compared to GPU, Sieve Type-3 provides 1.3× to 9.54× speedup and 6.60× to 18.43× energy reduction.

PCIe Standards and Queuing Depth. Since Type-2/3 is PCIe-integrated, we study how much latency overhead PCIe communication incurs. We use PCIe 4.0×16 in our simulation. Overall, it adds 4.6% to 6.7% communication overhead to the ideal case where k-mer matching requests are dispatched to the destination bank and subarray as soon as they arrive and returned to the host as soon as they complete. Reducing the number of PCIe lanes from 16 to 8, which reduces PCIe throughput, slows down Sieve by 24.8%.

Besides the PCIe features, the depth of the response ready queue (RRQ) (see section IV-C) also influences the communication overhead. We find that the optimal size for the RRQ is 340 to 680, just enough to make one or two PCIe Packet(s). This is because PCIe serializes packets and transfer them one by one. If the RRQ is too large, additional cycles are wasted on waiting for the queue to be filled, since the queue can only be drained at a constant rate of one PCIe packet at a time. If the RRQ is too small, extra cycles are wasted on constructing more PCIe packets as each packet contains fewer requests.

Figure 20:
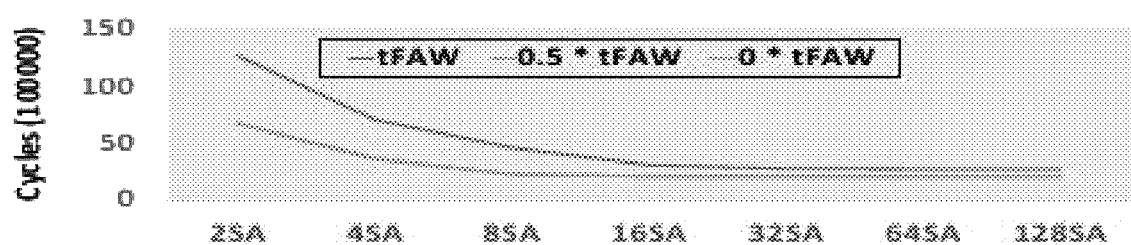
FIG. 20 illustrates speedup by relaxing a parameters that limits a rate of consecutive bank opening according to some embodiments.

DRAM Timing Parameters. DRAM timing parameters are generally overestimated, and relaxing them in a safe range typically increases the DRAM performance. To shed light on how these parameters affect Sieve, we demonstrate the impact of one parameter, tFAW, which limits the rate of consecutive bank opening. tFAW specifies a rolling temporal window in which four ACTIVATE commands can be issued to a rank. The fifth ACTIVATE has to wait until the tFAW countdown finishes. tFAW is primarily driven by power constraints, which is less of a concern for a PCIe-based system such as Sieve Type-2/3. FIG. 20 shows the speedup of a 32 GB Type-3 Sieve (with various subarray-level parallelism and averaged across all benchmarks) by relaxing tFAW. We make two observations: (1) relaxing tFAW by 50% almost doubles the k-mer matching throughput, which has the same effect as doubling the level of parallelism, and (2) further tFAW reduction gives no perceivable speedup even when we completely remove the tFAW constraint. We suspect another set of power-driven timing parameters called tRRD (tRRD L and tRRD S in DDR4) that specify the minimal DRAM cycles between two consecutive ACTIVATE become the bottleneck. Notice that, in FIG. 20, varying tFAW does not change the taper of subarray-level parallelism. It merely moves the curve up and down. Other ACTIVATE-related timing parameters such as tRAS and tRP, which are derived from hardware characteristics (e.g., wires' parasitic capacitance), are not recommended to be modified since changing them may interfere with safe operation (e.g., bits flip unexpectedly).

In this specification, there have been disclosed embodiments of the inventive subject matter and, although specific terms are employed, they are used in a generic and descriptive sense only and not for purposes of limitation. The following claims are provided to ensure that the present application meets all statutory requirements as a priority application in all jurisdictions and shall not be construed as limiting the scope of the inventive subject matter.

What is claimed:

1. An apparatus comprising:
    a plurality of memory cells addressable as rows and columns;
a plurality of matching circuits configured to be coupled to respective bit lines associated with the columns; and
    a control circuit configured to store respective reference sequences in respective ones of the columns, to sequentially provide rows of bits stored in the memory cells and bits of a query to the matching circuits, and to identify one of the reference sequences as corresponding to the query responsive to comparisons by the matching circuits, wherein each of the matching circuits comprises:
    an XNOR gate having a first input that receives column entries and a second input that receives bits of the query;
    an AND gate having a first input coupled to an output of the XNOR gate; and
    a latch having an input coupled to an output of the AND gate and an output coupled to a second input of the AND gate.

2. The apparatus of claim 1, wherein the plurality of memory cells comprises at least one subarray of a bank of a dynamic random access memory (DRAM).

3. The apparatus of claim 2, wherein the matching circuits are coupled to outputs of respective sense amplifiers that feed a row buffer of a subarray of the bank.

4. The apparatus of claim 2, wherein the bank comprises a plurality of interconnectable subarrays, each subarray having row buffer configured to be coupled to bit lines of an adjacent subarray, and wherein the matching circuits are coupled to a row buffer of one of the subarrays.

5. The apparatus of claim 1, wherein the control circuit is configured to terminate provision of rows to the matching circuits responsive to the matching circuits indicating that all of the references sequences lack at least one bit of the query.

6. The apparatus of claim 1, wherein the control circuit comprises respective segment evaluation circuits coupled to respective groups of the matching circuits and configured to generate respective match indicators for respective subgroups of each row of bits provided to the matching circuits and wherein the control circuit is configured to terminal provision of rows to the matching circuit responsive to the segment evaluation circuits.

7. The apparatus of claim 6, wherein the control circuit further comprises a plurality of secondary segment registers, respective ones of which receive and store the values received and stored by respective ones of the segment registers, and wherein the control circuit is configured to identify a column containing a reference sequence corresponding to the query responsive to the secondary segment registers.

8. The apparatus of claim 1, wherein the reference sequences comprise respective binary-encoded k-mer patterns.

9. An apparatus comprising:
    a plurality of memory cells addressable as rows and columns;
a plurality of matching circuits configured to be coupled to respective bit lines associated with the columns; and
    a control circuit configured to store respective reference sequences in respective ones of the columns, to sequentially provide rows of bits stored in the memory cells and bits of a query to the matching circuits, and to identify one of the reference sequences as corresponding to the query responsive to comparisons by the matching circuits,
    wherein the control circuit is configured to terminate provision of rows to the matching circuits responsive to the matching circuits indicating that all of the references sequences lack at least one bit of the query,
    wherein the control circuit comprises respective segment evaluation circuits coupled to respective groups of the matching circuits and configured to generate respective match indicators for respective subgroups of each row of bits provided to the matching circuits and wherein the control circuit is configured to terminate provision of rows to the matching circuit responsive to the segment evaluation circuits, and
    wherein each of the segment evaluation circuits comprises:
    a plurality of cascaded OR gates that receive inputs from respective ones of the matching circuits; and
    a segment register that receives and stores a value output from the plurality of cascaded OR gates and provides the stored output to another one of the segment evaluation circuits.

10. The apparatus of claim 9, wherein the control circuit is configured to latch values in the segment registers of the segment evaluation circuits during each cycle of a sequence of cycles in which the rows are provided to the matching circuits.

11. A method comprising:
    storing respective reference sequences in respective ones of columns of a plurality of memory cells addressable as rows and columns;
    sequentially providing rows of bits stored in the memory cells and bits of a query to a plurality of matching circuits coupled to respective bit lines associated with the columns; and
    identifying one of the reference sequences as corresponding to the query responsive to comparisons by the matching circuits,
    wherein each of the matching circuits comprises:
    an XNOR gate having a first input that receives column entries and a second input that receives bits of the query;
    an AND gate having a first input coupled to an output of the XNOR gate; and
    a latch having an input coupled to an output of the AND gate and an output coupled to a second input of the AND gate.

12. The method of claim 11, wherein the plurality of memory cells comprises a bank or a subarray of a bank of a dynamic random access memory (DRAM).

13. The method of claim 12, wherein the matching circuits are coupled to outputs of respective sense amplifiers that are coupled to respective bit lines of the bank or the subarray.

14. The method of claim 12, further comprising terminating presentation of rows to the matching circuits responsive to the matching circuits indicating that each of the references sequences lack at least one bit of the query.

15. The method of claim 14, further comprising respective segment evaluation circuits coupled to respective groups of the matching circuits generating respective match indicators for respective subgroups of the rows of bits.

16. The method of claim 15, wherein each of the segment evaluation circuits comprises:
    a plurality of cascaded OR gates that receive inputs from respective ones of the matching circuits; and a segment register that stores an output from the plurality of cascaded OR gates and provides the stored output to another one of the segment evaluation circuits.

17. The method of claim 16, further comprising latching values in the segment registers of the segment evaluation circuits during each row cycle.

18. The method of claim 11, wherein the plurality of memory cells comprises a memory chip and wherein the matching circuits are coupled to outputs of respective data I/O lines of the memory chip.

* * * * *

UNITED STATES PATENT AND TRADEMARK OFFICE
CERTIFICATE OF CORRECTION

| | | |
|---|---|---|
| PATENT NO. | : 11,776,594 B2 | Page 1 of 1 |
| APPLICATION NO. | : 17/462836 | |
| DATED | : October 3, 2023 | |
| INVENTOR(S) | : Skadron et al. | |

It is certified that error appears in the above-identified patent and that said Letters Patent is hereby corrected as shown below:

On the Title Page

Line 5 of the Abstract: Please correct "with the columns A control" to read -- with the columns. A control --

Signed and Sealed this
Twenty-eighth Day of November, 2023

Katherine Kelly Vidal
*Director of the United States Patent and Trademark Office*